United States Patent
Davenport et al.

(10) Patent No.: US 7,126,683 B2
(45) Date of Patent: Oct. 24, 2006

(54) DIRECT METHOD FOR THE CORRECTION OF PRESSURE INDUCED SCRAMBLING OF POLARIZED FLUORESCENCE INTENSITIES

(76) Inventors: Lesley Davenport, 219 Amboy Ave., # 9, Metuchen, NJ (US) 08840; Piotr Targowski, 27 Legionow Street, Apt. 1, Torun, 87-100 (PL)

( * ) Notice: Subject to any disclaimer, the term of this patent is extended or adjusted under 35 U.S.C. 154(b) by 0 days.

(21) Appl. No.: 11/241,412

(22) Filed: Sep. 30, 2005

(65) Prior Publication Data

US 2006/0132767 A1 Jun. 22, 2006

Related U.S. Application Data

(62) Division of application No. 09/659,412, filed on Sep. 11, 2000, now Pat. No. 6,956,646.

(60) Provisional application No. 60/153,488, filed on Sep. 11, 1999.

(51) Int. Cl.
G01J 3/30 (2006.01)
G01J 4/00 (2006.01)

(52) U.S. Cl. ...................... 356/317; 356/364

(58) Field of Classification Search ................ 356/317, 356/318, 364, 365; 250/458.1, 459.1, 461.1, 250/462.1
See application file for complete search history.

(56) References Cited

U.S. PATENT DOCUMENTS 5,322,794 A 6/1994 Davenport .................... 438/71
5,495,850 A 3/1996 Zuckerman .................. 128/634
5,626,134 A * 5/1997 Zuckerman .................. 600/317

OTHER PUBLICATIONS

Targowski et al., "Pressure Effects on Submicrosecond Phospholipid Dynamics Using a Long-Lived Fluorescence Probe", Journal of Fluorescence, vol. 8, No. 2, pp. 121-128 (1998).*
Targowski et al., "A Direct Method for the Correction of Pressure-Induced Scrambling of Polarized Fluorescence Intensities", Analytical Biochemistry, vol. 274, pp. 249-263 (1999).*
Markley, J.L. et al., "High Pressure Effects in Molecular Biophysics and Enzymology", Oxford Press, 1996.
Heremans, K, et al., *Biochim. Biophys. Acta.*, 1998, 1386, 353-370.
Gorovits, B.M., et al., *Biochemistry*, 1998, 37, 6132-6135.
Vidugiris, G.J., et al., *Biophys. J.*, 1998, 75, 463-470.
Valente-Mesquita, et al., *Biophys. J.*, 1998, 75, 471-476.
Silva, J.L, et al., *Biochemistry*, 1986, 25, 5780-5786.
Bernsdorff, C., et al., *Biphys. J.*, 1997, 72, 1264-1277.
Beney, L., et al., *Biphys. J.*, 1997, 72, 1258-1263.
Chong, L.G. et al., *Biochemistry*, 1983, 22, 5544-5550.
Targowski, P. et al., *J. Fluorescence*, 1998, 8, 121-128.

(Continued)

Primary Examiner—Hwa (Andrew) Lee
Assistant Examiner—Marissa J Detschel
(74) Attorney, Agent, or Firm—Michael P. Straher; Cozen O'Connor

(57) ABSTRACT

The present invention provides a simple and direct method for the simultaneous correction of steady-state polarized fluorescence intensities, depolarized (or scrambled) by the effects of applied hydrostatic pressure without having to first determine the scrambling factors from a separate experiment. The method involves direct recalculation of the measured polarized data obtained for the sample of interest at the time of data collection.

16 Claims, 8 Drawing Sheets

OTHER PUBLICATIONS

Sassaroli, M., et a., *Biophys. J.*, 1993, 64, 137-149.
Chong, L.G., et al., *Biochimica et Biophysica Acta.*, 1985, 813, 253-265.
Lin, M.C., *Biochemistry*, 1996, 10, 11846-11851.
Paladini, A.A., et al., *Rev. Sci. Instruments*, 1981, 52, 419-427.
Sire, O., et al., *Biphys. J.*, 1996, 70, 2903-2914.
Jablonski, A., *Bulletin de L' Academie Polonaise des Sciences*, 1960, 8, 259-264.
Chen, R.F., et al., *Science*, 1963, 147, 729-732.
Brand, L, et al., Spectroscopy and the Dynamics of Molecular Biological Systems, P.M. Bayley and R.E. Dale, editors, 1985, Academic Press, London, 259-305.
Beechem, J.M, et al., Topics in Fluorescence Spectroscopy: Principles, 1991, J.R. Lakowicz, ed., vol. 2, p. 241, Plenum, N.Y.
Davenport, et al., *Biophys. J.*, 1996, 71, 1837-1852.
Chong, L., et al., *Biochemistry*, 1983, 22, 409-415.
Chen, L.A., et al., *J. Biol. Chem.*, 1977, 252, 7500-7510.
Davenport, L., Methods in Enzymology, 278, L. Brand and J. Johnson, eds., 487-512, Academic Press.
Lentz, B.R., et al., *Biochemistry*, 1976, 15, 4529-4537.
McClare, C.W.F., *Anal. Biochem.*, 1971, 39, 527-530.
Weber, G., et al., *Trans. Farad. Soc.*, 1957, 53, 646-655.
Cantor, D.M., et al., *Applied Spectroscopy*, 1975, 29, 393-396.
Kawato, S., et al., *Biochemistry*, 1977, 16, 2319-2324.
Shurcliff, W.A., Polarized Light, 1962, Harvard Univ. Press, Cambridge, Mass.
Born, M., et al., Principles of Optics, wnd Ed., 1964, The MacMillan Company, N.Y. p. 554.
Crutzen, M., et al., *J. Phys. Chem.*, 1993, 97, 8133-8145.
Chryssomallis, G.S., et al., *Biochemistry*, 1981, 20, 3955-3959.
Davenport, et al., *J. Fluorescence*, 1995, 68, A303.
Davenport, et al., "Volume fluctuations in lipid bilayers: high pressure time-resolved fluorescence studies," Biophys. J. (1995) 68:A303 (X-Pos268).

* cited by examiner

| | Method of total intensity measurement | Excitation | Emission | $\langle r \rangle$ | Obtained intensity of fluorescence at $X(p=1\,bar)=0$ $Y(p=1\,bar)=0$ | Obtained intensity of fluorescence at $X(p=1.4\,kbar)=0.25$ $Y(p=1.4\,kbar)=0.10$ | Comments |
|---|---|---|---|---|---|---|---|
| 1 | photocurrent | fixed vertical polarizer | no polarizer | 0.1 | 1.00 | 0.92 | Not recommended even for non-pressure experiments, very instrument dependent |
| | | | | 0.36 | 1.16 | 1.014 | |
| 2 | photocurrent | unpolarized light | no polarizer | 0.1 | 1.00 | 0.997 | Less instrument dependent, but true non-polarized light is difficult to obtain |
| | | | | 0.36 | 0.96 | 0.95 | |
| 3 | Magic angle, Method 1 | fixed vertical polarizer | fixed polarizer at 55° to vertical | 0.1 | 1.00 | 0.983 | Recommended for non-pressure experiments |
| | | | | 0.36 | 1.00 | 0.937 | |
| 4 | Magic angle, Method 2 | fixed polarizer at 55° to vertical | fixed vertical polarizer | 0.1 | 1.00 | 1.013 | Recommended for non-pressure experiments |
| | | | | 0.36 | 1.00 | 1.045 | |
| 5 | Magic angle, Method 3 | depolarized light | fixed polarizer at 55° to horizontal | 0.1 | 1.00 | 0.995 | Recommended for non-pressure experiments, but true non-polarized light is difficult to obtain |
| | | | | 0.36 | 1.00 | 0.982 | |
| 6 | Magic angle, Method 4 | fixed polarizer at 55° to horizontal | scrambling plate | 0.1 | 1.00 | 0.988 | Recommended for non-pressure experiments |
| | | | | 0.26 | 1.00 | 0.955 | |
| 7 | calculated with formula: $G \cdot i_{VV} + 2 \cdot i_{VH}$ | fixed vertical polarizer | rotating polarizer | 0.1 | 1.00 | 0.98 | Recommended for non-pressure experiments, $G$ must be known |
| | | | | 0.36 | 1.00 | 0.94 | |

| | Method of total intensity measurement | Excitation | Emission | $\langle r \rangle$ | Obtained intensity of fluorescence at | | Comments |
|---|---|---|---|---|---|---|---|
| | | | | | $X(p=1\text{bar})=0$ $Y(p=1\text{bar})=0$ | $X(p=1.4\text{ kbar})=0.25$ $Y(p=1.4\text{ kbar})=0.10$ | |
| 8 | calculated with formula: $\dfrac{i_{HH} \cdot i_{VV} + 2 \cdot i_{VH}}{i_{HV}}$ | rotating polarizer | rotating polarizer | 0.1 | 1.00 | 0.96 | Recommended for non-pressure experiments, definitely wrong for pressure domain |
| | | | | 0.36 | 1.00 | 0.83 | |
| 9 | Calculated with equation (6) | rotating polarizer | rotating polarizer | 0.1 | 1.00 | 1.00 | Recommended for pressure domain experiments, $G$ and $E$ factors must be known |
| | | | | 0.36 | 1.00 | 1.00 | |

FIGURE 5B

DIRECT METHOD FOR THE CORRECTION OF PRESSURE INDUCED SCRAMBLING OF POLARIZED FLUORESCENCE INTENSITIES

CROSS REFERENCE TO RELATED APPLICATIONS

This application is a divisional of U.S. application Ser. No. 09/659,412, filed Sep. 11, 2000 now U.S. Pat. No. 6,956,646, which claims benefit of U.S. Provisional Application Ser. No. 60/153,488, filed Sep. 11, 1999, the content of which is incorporated by reference herein in its entirety.

FIELD OF THE INVENTION

The present invention is directed to methods for the direct and simultaneous correction of steady-state polarized fluorescence intensities, depolarized (or scrambled) by the effects of applied hydrostatic pressure. The present methods eliminate the requirement of first determining the scrambling factors from a separate experiment with a dye immobilized in a rigid medium. Rather, in accordance with the present methods, correction for depolarizing effects of windows under a pressure differential, such as high pressure spectroscopy cell windows, is achieved by direct recalculation of the measured polarized data obtained for the sample of interest at the time of data collection. The methods of the invention can be used for the correction of steady-state polarized data, and are also easily adapted for use in time-resolved polarized fluorescence measurements.

BACKGROUND OF THE INVENTION

The combination of applied hydrostatic high pressure with polarized steady state fluorescence spectroscopy can provide important insights into altered conformation, dynamics and interactions of complex biological macromolecules in solution (See reference 1, infra.). Due to the non-compressibility of the aqueous solvent, applied pressure effects on the observed fluorescence emission anisotropy reflect exclusive alteration in the hydrodynamic volume of the system under investigation. Hence, protein conformations (See reference 1–4, infra.), dissociation and association of oligomeric proteins (See references 1,5,6, infra.), and altered lipid membrane structure (See reference 1,7–9 infra.) and/or dynamics (See references 10–12, infra.), can be readily studied at concentration levels of non infinite dilution. In addition, the technique can provide information regarding local flexibility or overall rotational dynamics of a system, depending on the nature of the fluorophore studied (See reference 1, 2, 4, 13, infra.).

However, a severe limitation of this approach is the inherent scrambling of the polarized light by the induced birefringence of the optical windows (quartz or to a lesser extent, sapphire) of the spectroscopy cell when pressures of greater than 0.2 kbar are applied. At pressures greater than 1 kbar, this so-called "scrambling" effect can be on the order of the measured fluorescence anisotropy. As a result, measured polarized fluorescence intensities are contaminated by scrambling artifacts, and determined values of the fluorescence emission anisotropy (EA) are significantly distorted.

In this regard, several approaches have been adopted for correction of measured polarized fluorescence pressure data. Paladini and Weber (See reference 14, infra.), using a well-characterized rotationally immobile fluorophore in glycerol at low temperatures, determined values for the scrambling correction factor ($\alpha(p)$) as a function of increasing hydrostatic pressure, under the same optical conditions (i.e. excitation and emission wavelengths) as for the fluorophore of interest. Since the probe is rotationally restricted, deviations of <r> from that measured at zero pressure value directly reflect the combined depolarizing artifacts comprising scrambling effects of the optical windows and possible internal light reflections within the high pressure spectroscopy cell. Once scrambling factors have been determined, values of <r> for the measured system at any pressure can now be corrected. This method whilst effective, necessitates a separate experiment using a standard fluorophore system in order to determine values for the scrambling factors, $\alpha(p)$. Additionally, due to aging of the optical windows of the high pressure cell with applied hydrostatic pressure, values for $\alpha(p)$ can change between experiments, and should strictly be recorded for each experiment performed.

An alternate mechanical approach is to exclude possible scrambling artifacts by mounting the excitation and emission polarizers between the optical windows of the bomb and the sample cuvette, inside the high pressure spectroscopy cell (See reference 15, infra.). However, this approach is experimentally challenging as the polarizing material must be sandwiched between quartz plates, and sealed to exclude possible deleterious effects of the pressure transducing fluid (usually ethanol). Additionally, unless a rotating polarizer with remote access can be incorporated within the high pressure spectroscopy cell, T-format optics are required with simultaneous collection of vertical and horizontal emission paths for polarized measurements. This approach can lead to instrumental problems involving the matching of the photomultiplier responses of the two detection arms, or alternatively requires the use of optical fibers to transmit emission intensities from the high pressure spectroscopy cell via more conventional L-configuration optics.

It can be seen that there exists a need for methods that address the shortcomings of approaches discussed above. The present invention is directed to this important end.

SUMMARY OF THE INVENTION

In some preferred embodiments, the present invention provides methods for the extraction of true values of emission anisotropy ($<r>_{corr}$) from fluorescence intensities obtained for a sample under an applied hydrostatic pressure (p), comprising the steps of measuring polarized fluorescence intensities and then determining excitation and emission correction factors.

Preferably, the true values of emission anisotropy are obtained from said fluorescence intensities without performing a separate pressurized calibration experiment, and in some more preferred embodiments, the excitation correction factor X and said emission correction factor Y are determined for a given pressure (p) from said fluorescence intensities substantially according to the equations:

$$X(p) = \frac{G \cdot i_{HV} - iHH}{G \cdot i_{HV} - i_{HH} + E \cdot (G \cdot i_{VV} - i_{VH})} \quad (12)$$

and:

$$Y(p) = \frac{E \cdot i_{VH} - iHH}{E \cdot i_{VH} - i_{HH} + G \cdot (E \cdot i_{VV} - i_{HV})} \quad (13)$$

wherein $i_{VV}$, $i_{VH}$, $i_{HH}$, and $i_{HV}$ represent the measured and pressure induced distorted polarized intensities for the sample of interest, and E and G, are both sample and pressure independent instrument factors characteristic for the chosen excitation and emission wavelength conditions.

In some preferred embodiments, the E-factor corrects for unequal sensitivity of the detection system to the vertical and horizontal polarized excitation light, the G-factor corrects for unequal sensitivity of the detection system to the vertical and horizontal polarized emission light, and said E and G factors are determined at atmospheric pressure according to the equations:

$$G = \frac{i_{HH_0}}{i_{HV_0}} \quad (14)$$

and $$E = \frac{i_{HH_0}}{i_{VH_0}}$$

where said $i_{VH0}$, $i_{HH0}$, and $i_{HV0}$ are polarized fluorescence intensities obtained at atmospheric pressure.

In some preferred embodiments, the methods of the invention further comprise the use of said excitation and emission correction factors to detect abnormalities in an optical window.

In some particularly preferred embodiments, said true values of emission anisotropy ($<r>_{corr}$) are obtained from the equations:

$$<r>_{corr} = \frac{R-1}{R+2-3 \cdot (X+Y-X \cdot Y+R \cdot Y-R \cdot X \cdot Y)}; \quad (11)$$

$$R = G \cdot \frac{i_{VV}}{i_{VH}}$$

Some further more preferred embodiments further comprise determining corrected total intensities ($S_{corr}$) in accordance with the following formula:

$$S_{corr} = G \cdot \frac{1-3 \cdot (Y-X \cdot Y)}{1-X-2 \cdot (Y-X \cdot Y)} \cdot i_{VV} \pm \frac{2-3 \cdot (X+Y-X \cdot Y)}{1-X-2 \cdot (Y-X \cdot Y)} \cdot i_{VH} \quad (15)$$

also provided in accordance with the invention are methods for the extraction of corrected values of total intensities ($S_{corr}$) from fluorescence intensities obtained for a sample under an applied hydrostatic pressure (p), comprising the steps of measuring polarized fluorescence intensities and then determining excitation and emission correction factors. Preferably, the corrected total intensities ($S_{corr}$) are obtained from said fluorescence intensities without performing a separate pressurized calibration experiment. Also preferably, the excitation correction factor X and said emission correction factor Y are determined for a given pressure (p) from said fluorescence intensities substantially according to the equations for X and Y, supra, and the values for E and G are determined at atmospheric pressure according to the equations provided supra.

In preferred embodiments, the invention provides methods for measuring and removing scrambling effects, induced by an applied hydrostatic pressure (p), from fluorescence intensities while avoiding the need for a separate pressurized calibration experiment, comprising the acts of measuring polarized fluorescence intensities and then determining excitation and emission correction factors simultaneously.

Some preferred embodiments of the methods of the invention further comprise determining a steady state fluorescence emission anisotropy value ($<r>_{corr}$).

In further preferred embodiments, methods are provided for obtaining the true difference in polarized fluorescence intensities (D) from fluorescence intensities obtained for a sample under an applied hydrostatic pressure (p), comprising the steps of measuring polarized fluorescence intensities and then determining excitation and emission correction factors, preferably without performing a separate pressurized calibration experiment.

In some preferred embodiments, methods are provided for obtaining true values of emission anisotropy ($<r>_{corr}$) from fluorescence intensities obtained for a sample under an applied hydrostatic pressure (p), comprising the steps of:

a) measuring polarized fluorescence intensities from a sample of interest under a preselected hydrostatic pressure;

b) calculating excitation and emission correction factors G and E where $G(p) = i_{HH}/i_{HV}$ and $E(p) = i_{HH}/i_{VH}$, where non-scrambling conditions are constant for given instrument and where G describes the difference in instrument sensitivity for given instrument to polarizations of emitted fluorescence light, and E describes the difference in instrument sensitivity for given instrument to polarizations of excitation light;

where $i_{HH}$, $i_{HV}$ and $i_{VH}$ are polarized fluorescence intensities obtained with excitation and emissions polarizers having the indicated orientation; and wherein said true values of emission anisotropy are obtained from said fluorescence intensities without performing a separate pressurized calibration experiment.

In further preferred embodiments, methods are provided for the correction of time dependent polarized fluorescence intensities obtained for a sample under an applied hydrostatic pressure (p), comprising the steps of:

a) collecting four non-truncated polarized ($i_{VV}$, $i_{VH}$, $i_{HH}$, $i_{HV}$) decay profiles;

b) integrating said decay profiles;

c) calculating emission and excitation correction factors X and Y, respectively, from integrals of said profiles; and d) using said emission and excitation factors, together with said $i_{VV}$ and $i_{VH}$ decay profiles, to perform a sum-difference analysis to obtain profiles for total corrected intensity ($S_{corr}$) and difference in polarized fluorescence intensity ($D_{corr}$); preferably without performing a separate pressurized calibration experiment.

Also provided by the present invention are computer readable storage medium comprising computer executable code for instructing a computer-controlled instrument to perform the acts of measuring polarized fluorescence intensities and then determining excitation and emission correction factors, preferably wherein said emission correction factor Y are determined for a given pressure (p) from said fluorescence intensities substantially according to the equations:

$$X(p) = \frac{G \cdot i_{HV} - i_{HH}}{G \cdot i_{HV} - i_{HH} + E \cdot (G \cdot i_{VV} - i_{VH})} \quad (12)$$

and:

$$Y(p) = \frac{E \cdot i_{VH} - i_{HH}}{E \cdot i_{VH} - i_{HH} + G \cdot (E \cdot i_{VV} - i_{HV})} \quad (13)$$

wherein $i_{VV}$, $i_{VH}$, $i_{HH}$, and $i_{HV}$ represent the measured and distorted polarized intensities for the sample of interest, and E and G, are both sample and pressure independent instrument factors characteristic for the chosen excitation and emission wavelength conditions, and more preferably wherein the E-factor for unequal sensitivity of the detection system to the vertical and horizontal polarized excitation light, the G-factor corrects for unequal sensitivity of the detection system to the vertical and horizontal polarized emission light, and said E and G factors are determined at atmospheric pressure according to the equations:

$$G = \frac{i_{HH_0}}{i_{HV_0}} \quad (14)$$

and $$E = \frac{i_{HH_0}}{i_{VH_0}}$$

where said $i_{VH_0}$, $i_{HH_0}$, and $i_{HV_0}$ are polarized fluorescence intensities obtained at atmospheric pressure.

In some preferred embodiments, the computer readable storage medium further comprises computer executable code enabling the use of said excitation and emission correction factors to detect abnormalities in an optical window.

Preferably, the computer readable storage medium provides said true values of emission anisotropy without performing a separate pressurized calibration experiment.

In some preferred embodiments, the computer readable storage medium further comprising determining corrected total intensities ($S_{corr}$) in accordance with the 5 following formula:

$$S_{corr} = G \cdot \frac{1 - 3 \cdot (Y - X \cdot Y)}{1 - X - 2 \cdot (Y - X \cdot Y)} \cdot i_{VV} + \frac{2 - 3 \cdot (X + Y - X \cdot Y)}{1 - X - 2 \cdot (Y - X \cdot Y)} \cdot i_{VH} \quad (15)$$

Also provided in accordance with the methods of the invention are computer-controlled instruments for measuring and removing scrambling effects, induced by an applied hydrostatic pressure (p), from fluorescence intensities while avoiding the need for a separate calibration experiment, comprising a computer/processor, a fluorescence spectrometer, and a computer readable storage medium comprising computer executable code for instructing the instrument to perform the acts of measuring polarized fluorescence intensities and then determining excitation and emission correction factors.

In accordance with some preferred embodiments of the present invention, methods are provided for correction of time resolved or steady state polarized fluorescence intensities that have been depolarized (i.e., "scrambled") by the effects of pressure, wherein measured polarized fluorescence intensities are directly recalculated without having to perform a further calibration experiment.

In some preferred embodiments, the measured polarized fluorescence intensities are directly recalculated at the time of data collection. Preferably, the methods comprise measuring polarized fluorescence intensities and recalculating the measured intensities in accordance with equations 6 and/or 7, infra.

In more preferred embodiments, methods are provided for the correction of steady-state polarized fluorescence intensities that have been depolarized (i.e., "scrambled" ) by the effects of applied hydrostatic pressure comprising the steps of measuring steady-state polarized fluorescence intensities and recalculating the measured intensities in accordance with equation 6 and/or 7, infra.

In further preferred embodiments, methods are provided for the correction of time resolved polarized fluorescence intensities that have been depolarized (i.e., "scrambled") by the effects of hydrostatic pressure comprising the steps of measuring time resolved polarized fluorescence intensities and using sum and difference analyses of time correlated single-photon polarized decay profiles in conjunction with equations 6 and/or 7, infra.

Also provided in accordance with the present invention are methods for the detection of abnormalities in an optical window, preferably a high pressure spectroscopy cell window, comprising the steps of obtaining polarized fluorescence data through said window; calculating a scrambling correction factor;

resolved the scrambling factor into the two contributing components X and Y, and detecting anomalous alterations in the values of said X or Y.

Also provided are methods for correction for depolarizing effects of optical windows under a pressure differential comprising recalculating measured polarized fluorescence intensities in accordance with equations 6 and/or 7, infra. In some preferred embodiments, the optical window is in a high pressure spectroscopy cell. In further preferred embodiments, wavelength-dependent correction factors are obtained separately for the excitation ($X(p,\lambda)$) and emission ($Y(p,\lambda)$) optical windows.

In some particularly preferred embodiments, the methods of the invention are 20 used to correct depolarized steady-state or time resolved polarized fluorescence intensities arising from fluorophores in a sample of interest.

Also provided in accordance with the present invention are computing devices having programming that results in performance of a calculation according to the invention (e.g., equations 6 and/or 7, supra), and instruments for measuring fluorescence intensities comprising the computing devices. In one preferred embodiment, the present invention provides instruments, preferably flourescence spectrometers, that contain. computing devices having programming that results in performance of a calculation according to the invention, and instrument-computer combinations that have programming that results in performance of a calculation according to the invention.

In a further aspect, the present invention also includes software that performs calculations according to the methods of the invention disclosed herein, and in particular, equations 2–7, supra.

BRIEF DESCRIPTION OF THE FIGURES

FIGS. 5A and 5B describe simulation studies showing the influence of changes in sample emission anisotropy, r, and of applied hydrostatic pressure induced scrambling on total intensity measurements determined via varying methods. The value for the total intensity, i, measured at r=0.1 and atmospheric pressure was assigned an arbitrary value of 1.0 for all the methods. The ranges for the r, X and Y changes are representative of data presented in the FIG. 4.

DETAILED DESCRIPTION

Figure 1:
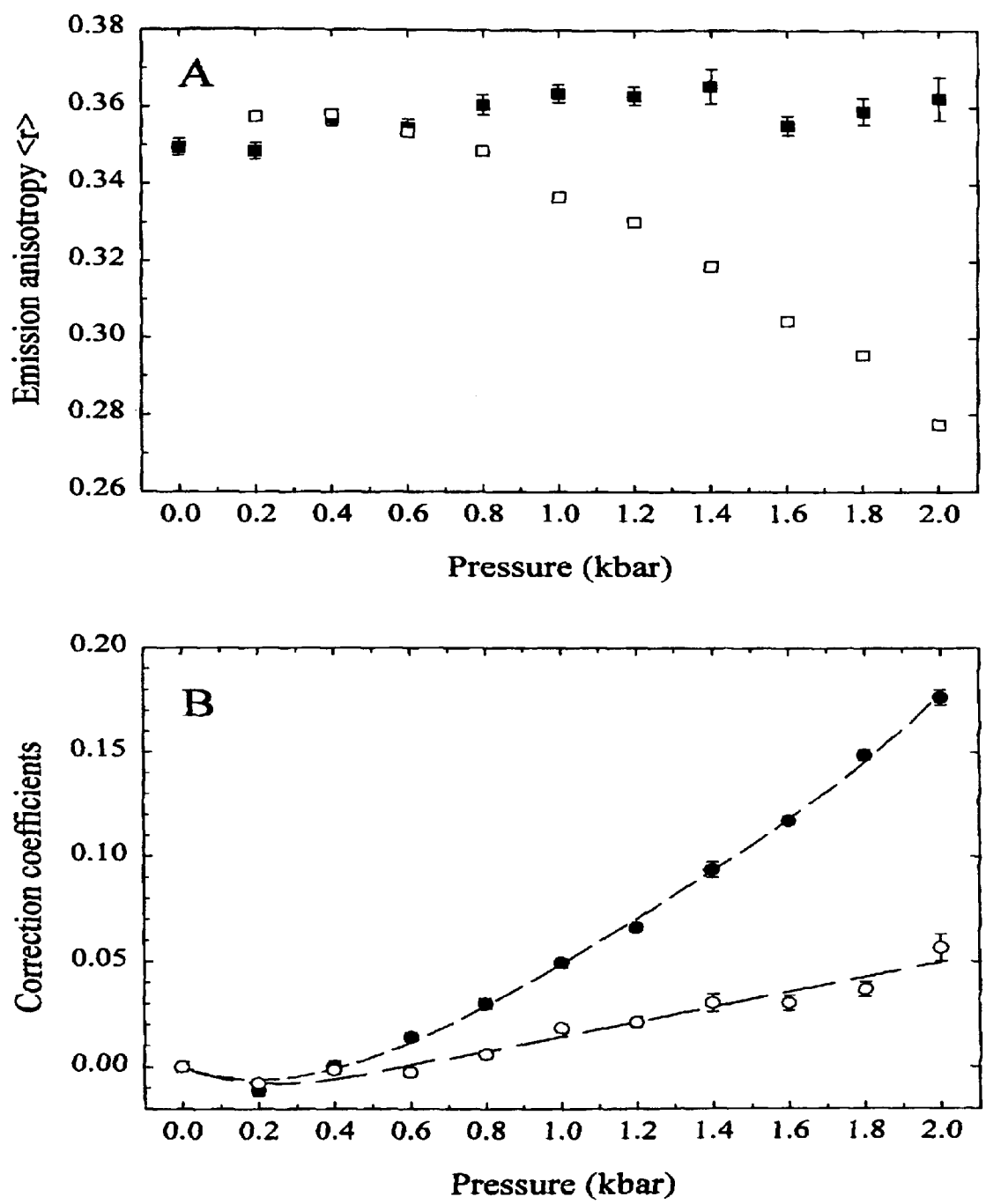
FIG. 1 shows DPH in glycerol (4 μM) at 20° C. Panel A: Steady-state emission anisotropy (<r>) as a function of increasing hydrostatic pressure: (□—□) uncorrected data calculated according to Equation (1); (■—■) data corrected using the direct method. Panel B: Excitation, $X(P)_{340\ nm}$, (●—●) and emission, $Y(P)_{448\ nm}$, (○—○) correction factors as a function of increasing hydrostatic pressure. Values for the excitation (E=0.9763±0.0027) and grating (G=1.9137±0.0043) factors were determined from this experiment assuming X(p=1 bar)=0 and Y(p=1 bar)=0. Excitation was 340 nm and emission detected at 448 nm, with corresponding bandwidths of 4 nm each, respectively. Calculated errors were not greater than 0.005.

In one aspect, the present invention provides methods are provided for correction of time resolved or steady state polarized fluorescence intensities that have been depolarized (i.e., "scrambled") by the effects of pressure, wherein measured polarized fluorescence intensities are directly recalculated without having to perform a further calibration experiment. In some preferred embodiments, the methods are used to correct polarized fluorescence intensities that have been obtained from a time resolved or steady state spectrofluorometer, having or being used in conjunction with a high pressure spectroscopy cell.

The present methods provide an alternate approach for the correction of polarized pressure data. Unlike other known methods, the correction is applied directly on the experimentally obtained polarized intensity data and eliminates the need for a second 'calibration' experiment. Additionally, wavelength-dependent correction factors are obtained separately for the excitation (X(p,λ)) and emission (Y(p, λ)) optical windows. Hence, no mechanical alterations to the experimental fluorescence set-up is required. The present methods provide the additional advantage of affording detection of damage (e.g. cracking) to a window, such as that which can occur during the course of an experiment. Thus, in accordance with preferred embodiments of the invention, methods are provided for the detection of such damage.

Using conventional right-angle optical geometry and vertically polarized excitation light, the steady-state emission anisotropy, <r>, may be calculated from the difference (D) divided by the sum (S) of polarized intensities (See reference 14, infra.):

$$<r> = \frac{D}{S} = \frac{G \cdot i_{VV} - i_{VH}}{G \cdot i_{VV} + 2 \cdot i_{VH}} = \frac{R-1}{R+2}; \quad (10)$$

$$R = G \cdot \frac{i_{VV}}{i_{VH}};$$

$$G = \frac{i_{HH}}{i_{HV}}$$

where G represents the grating factor, which corrects for unequal sensitivity of the detection system for horizontal and vertically polarized emissions (See reference 17, infra.). The first subscript, V or H, refers, respectively, to the vertical or horizontal orientation of the dielectric vector of the excitation and the second to those for emission.

The degree of depolarization of the excitation and emitted light, resulting from pressure dependent birefringence effects on the quartz (or sapphire) windows of the high pressure spectroscopy cell, may be represented by the factors X(p) and Y(p), respectively. Under such conditions Equation 1 is now invalid due to loss of the vertical alignment of the polarized excitation light. Furthermore, the resultant polarized fluorescence signals are also depolarized. The correct steady state fluorescence emission anisotropy value, $<r>_{corr}$, can however, be recovered for a given applied hydrostatic pressure, from the following expression (see Example 2 for the derivation):

$$<r>_{corr} = \frac{R-1}{R+2-3 \cdot (X+Y-X \cdot Y+R \cdot Y-R \cdot X \cdot Y)}; \quad (11)$$

$$R = G \cdot \frac{i_{VV}}{i_{VH}}$$

where the excitation (X) and emission (Y) scrambling factors for a given pressure are defined respectively, as:

$$X(p) = \frac{G \cdot i_{HV} - i_{HH}}{G \cdot i_{HV} - i_{HH} + E \cdot (G \cdot i_{VV} - i_{VH})} \quad (12)$$

and:

$$Y(p) = \frac{E \cdot i_{VH} - i_{HH}}{E \cdot i_{VH} - i_{HH} + G \cdot (E \cdot i_{VV} - i_{HV})} \quad (13)$$

Here, the quantities $i_{VV}$, $i_{VH}$, $i_{HH}$, and $i_{HV}$ represent the measured and distorted polarized intensities for the sample of interest. The instrumental quantities E and G, are both sample and pressure independent and are characteristic for the chosen excitation and emission wavelength conditions. Here, the E-factor corrects for any inequality in the intensities of the vertical and horizontal polarized excitation light.

$$G = \frac{i_{HH_0}}{i_{HV_0}} \text{ and } E = \frac{i_{HH_0}}{i_{VH_0}} \quad (14)$$

Values for the parameters E and G are determined experimentally at atmospheric pressure (denoted by the zero subscript) using one of two methods described in the Data Analysis section. The appropriate scrambling factors, X(p) and Y(p), required for pressure-dependent emission anisotropy measurements can thus be fully characterized for the chosen sample of interest and the particular high pressure spectroscopy cell.

Extraction of total intensity data [$S = G \cdot i_{VV} + 2 \cdot i_{VH}$] from polarized intensity measurements ($i_{VV}$, $i_{VH}$, $i_{HH}$, and $i_{HV}$), are similarly distorted by pressure-induced birefringence effects. For such conditions, the corrected formula for total intensities measured under pressure is now defined (see Example 2 for derivation):

$$S_{corr} = G * \frac{1 - 3 \cdot (Y - X \cdot Y)}{1 - X - 2 \cdot (Y - X \cdot Y)} \cdot i_{VV} + \frac{2 - 3 \cdot (X + Y - X \cdot Y)}{1 - X - 2 \cdot (Y - X \cdot Y)} \cdot i_{VH} \quad (15)$$

Similarly, the difference (D) in polarized intensities, which includes an anisotropy term (Equation 1) [$D_{corr} = S_{corr} \cdot r_{corr}$ ($\equiv G \cdot i_{VV} - i_{VH}$ for non-scrambling conditions)], may also be corrected for birefringence artifacts and re-expressed as:

$$D_{corr} = G * \frac{1}{1 - X - 2 \cdot (Y - X \cdot Y)} \cdot i_{VV} + \frac{1}{1 - X - 2 \cdot (Y - X \cdot Y)} \cdot i_{VH} \quad (16)$$

It is clear that Equations (6) and (7) can be adopted for the analysis of time-dependent polarized pressure data (r(t,p)) using sum and difference analyses of time-correlated single-photon polarized decay profiles. (For a discussion of this general data analysis approach, see reference 18, infra.). In contrast, direct correction of measured polarized decay profiles [$i_V(t,p)$ and $i_H(t,p)$] collected under pressure and analyzed using vector analysis in combination with global methodologies (See reference 19, infra.) has been discussed elsewhere (See reference 20, infra.). Correction of polarized pressure-dependent phase and modulation lifetime data, have been described previously by Chong and Cossins (See reference 21, infra.).

In addition, it will be apparent that Equations (6) and (7) can be adapted for the analysis of time-dependent polarized fluorescence data (r(t,p)) using vector analysis of time-correlated single-photon polarized decay profiles, for example by using the following equations:

$i_{VVCORR} = G \cdot \{(1-Y+X \cdot Y)/[1-X-2 \cdot (Y-X \cdot Y)]\} i_{VV} + \{(-X-Y+X \cdot Y)/[1-X-2 \cdot (Y-X \cdot Y)]\} \cdot i_{VH}$ $i_{VHCORR} = G \cdot [-Y/(1-2 \cdot Y)] \cdot i_{VV} + [(1-Y)/[1-(2 \cdot Y)] \cdot i_{VH}$ Often total fluorescence intensities are measured after removal of the polarizers from the instrument. However, the more correct approach involves>magic angle=polarizer geometries (See reference 16, infra.). Four such polarizer orientations may be adopted:

Method 1: Using vertically polarized excitation light combined with the emission polarizer oriented at $$54.74° \left[\equiv arcos\left(\frac{1}{\sqrt{3}}\right)\right]$$

to the vertical.

Method 2: Excitation light oriented 54.74° to the vertical with the emission polarizer oriented vertically.

Method 3: 'Natural' or unpolarized excitation light in combination with the emission polarizer oriented at 54.74° to the horizontal.

Method 4: Linearly polarized excitation light oriented 54.74° to the horizontal and a 'scrambling' plate (such as a quarter-wave plate), which ensures that G=1, in the emission train.

For all cases, the measured emission light intensity $(i(F)_{obs})$ is precisely proportional to the total fluorescence and is independent of the fluorescence emission anisotropy. However, for pressure dependent measurements, the situation is made complicated. The measured signal is now dependent on the emission anisotropy (r) and hence does not reflect the true total fluorescence.

In the case of Method 1, the observed>magic angle=intensity, $i(F)_{obs}$, is distorted from the true fluorescence intensity, $i(F)_{true}$, by the factor (see Example 2, Equation A.15, for the derivation):

$$i(F)_{obs} = i(F)_{true} \cdot [1-(X-Y+X \cdot Y) \cdot r] \quad (17)$$

Whereas for the second 'magic angle' condition, (Method 2) the observed fluorescence intensity is distorted by the factor (see Example 2, Equation. A.16):

$$i(F)_{obs} = i(F)_{true} \cdot [1+(X-Y-X \cdot Y) \cdot r] \quad (18)$$

For Method 3, the error factor depends only, as expected, on polarization scrambling at emission window (see Example 2, Equation A.17):

$$i(F)_{obs} = i(F)_{true} \cdot \left[1 - \frac{1}{2} \cdot Y \cdot r\right] \quad (19)$$

And similarly for Method 4 (see Example 2, Equation A.18):

$$i(F)_{obs} = i(F)_{true} \cdot [1 - \frac{1}{2} \cdot X \cdot r] \quad (20)$$

In practice, the error terms introduced by the factors defined via Equations (8)–(11) are proportional to r. Consequently they are small and sometimes negligible.

As used herein, the term "DPA" denotes 9,10-diphenylanthracene; "DPH" denotes 1,6-diphenyl-1,3,5-hexatriene; "DPPC" denotes L-α-dipalmitoylphosphatidylcholine; "EA" denotes fluorescence emission anisotropy; "HEPES" denotes N-2-hydroxyethylpiperazine-N'-2-ethanesulfonic acid; "HPSC" denotes high pressure spectroscopy cell; "$P_m$" denotes lipid phase transition pressure; "SUVs" denotes small unilamellar vesicles; "$T_c$" denotes lipid phase transition temperature; and "TLC" denotes thin-layer chromatography.

It will be recognized that correction of experimentally measured time-correlated single photon counting decay data also can be obtained by the methods of the invention.

It is important to note that total intensity fluorescence profiles are also affected to a varying extent by pressure induced scrambling effects which exhibit wavelength dependence. From simulation studies, we have observed that even so-called "magic angle" intensity approaches (See reference 16, infra.) can result in contaminated 'total' intensity values. Thus, in a further aspect of the present invention, methods for correcting total fluorescence intensity measurements, constructed from the polarized components $i_{VV}$ and $i_{VH}$ is disclosed herein.

The present invention provides alternative and more convenient methods for the correction of pressure dependent steady-state polarized fluorescence intensity data, which experimentally is artificially depolarized due to pressure induced birefringence effects on the quartz optical windows of, for example, a high pressure spectroscopy cell. While for quartz windows the induced scrambling effect is less than when compared with sapphire, the magnitude of the scrambling effect can still be on the order of calculated EA values (See reference 28, infra.).

A significant advantage of the direct approach described herein lies in the fact that both excitation and emission correction factors are determined at the time of collection of measured polarized fluorescence intensities required for determining the EA of the sample of interest. As such, a second calibration experiment is not needed, minimizing risks of unnecessary pressurizing of the optical windows of the high pressure spectroscopy system. This is significant, as correction curves can vary considerably with the number of pressurization procedures (and in our experience vary from day-to-day; data not shown) and with the wavelength conditions used for the experiment, as demonstrated here. Hence, in practice, a correction curve is required for each polarized pressure experiment performed using the 'indirect' experimental approach.

The correction curve used in the indirect approach is traditionally constructed using a fluorescent sample which demonstrates both a high fluorescence emission anisotropy (often achieved by measuring highly viscous samples at cold temperatures (See reference 9, 14, infra. )), and which matches the excitation and emission conditions for the test sample. Furthermore, the standard employed should preferentially demonstrate a large Stokes shift, in order to obviate reabsorption of emitted light (secondary inner filter effect). In practice, finding the appropriately polarized fluorescent standard, in combination with working in glycerol, is often inconvenient. Care must be taken to ensure that no microcrystals of the fluorescent dye are present which often necessitates stirring overnight. In addition, introduction of the glycerol sample and subsequent sealing of the cylindrical cuvette required for high pressure measurements, is often tedious and time consuming. Furthermore, the spectroscopic effect of reduced temperatures on the optical windows of the high pressure spectroscopy cell is uncertain. For the direct method excitation and emission correction factors are obtained at the temperature of the experiment, and are applied directly to the individual polarized intensities, in contrast to the indirect method where the value of $<r>_{uncorr}$ is corrected to the expected $r_0$ value. In our experience, most often the experimentally determined value for the EA obtained for the immobilized dye at atmospheric pressure is not equal to the expected $r_0$ value. Deviations may result from reflections within the high pressure spectroscopy cell. Consequently, in the determination (Equation 12) of the scrambling factor ($\alpha(p)$), values for $<r>_{p=1}$ were taken to be equal to $<r>_{true}$ measured for viscous systems. For the direct correction approach, such approximations are not necessary. Any intrinsic properties of the HPSC are accounted for in the separate determination of the E and G-factors (Equation 5).

The direct approach provides for separation of the average correction factor ($\alpha(p)$) from the indirect approach into individual excitation ($X(p)$) and emission ($Y(p)$) components. As shown, most often values for $X(p)$ and $Y(p)$ are not equal in magnitude for a given pressure, and are intimately dependent on the applied hydrostatic pressure, with their effect increasing significantly at $p>0.6$ kbar. Additionally, we have found that values for $X(p)$ and $Y(p)$ are dependent on the emission or excitation wavelengths, respectively, although as expected, are independent of the fluorescent sample.

An important and surprising discovery disclosed herein is the presence of hysteresis in the response of the correction factors to increasing and decreasing applied pressure. This result questions the validity of polarized data collected with decreasing applied pressure, that has been corrected by the indirect method using values for $\alpha(p)$ derived from increasing pressure effects. Suspected hysteresis effects of the sample may be contaminated by the application of inappropriate $\alpha(p)$ values.

Our total intensity simulation studies shows that significant errors are introduced when standard methods for measurements of total fluorescence intensity values are used in combination with pressure domain experiments, particularly when using highly polarized samples. Interestingly, the smallest errors result when unpolarized excitation light is used in combination with appropriate 'magic angle' polarizer conditions on the emission side (Method 3). However, as discussed, it is often technically more difficult to precisely obtain non polarized excitation light. Consequently, if a good scrambling plate is available, Method 4 (FIG. 5A, condition 6) appears to provide an excellent compromise between systematic error and experimental complication. This conclusion is most important when performing pressure dependent time dependent decay measurements. Here such errors can lead to resolution of additional "artificial" decay components during data analysis. Again, such practical uncertainties may be avoided and scrambling artifacts removed, if the appropriate mathematical correction procedure (equation 6) and experimental set-up is utilized for polarized fluorescence pressure studies.

In one aspect, the present invention provides methods for the detection of abnormalities in an optical window. The window can be any that is subject to a pressure gradient, and which produced a depolarization of fluorescence intensities. Thus, the methods of the invention are applicable to a variety of applications, including but not limited to windows used in deep-sea applications such as those in submarines, deep-sea exploration vehicles, and deep-sea devices. In a further aspect of the invention, the disclosed methods are used for inspecting or monitoring such windows for potentially dangerous abnormalities that could be indicative of imminent failure. In some preferred embodiments, the methods of the invention are useful for the detection of abnormalities in optical windows used in fluorescence spectroscopy, for example quartz and sapphire windows used in high pressure spectroscopy cells.

Also provided in accordance with the present invention are computing devices having programming that results in performance of a calculation according to the invention (e.g., equations 6 and/or 7, supra), and instruments for measuring fluorescence intensities comprising the computing devices. Computing devices are any device or collection of devices that alone or together contain programming that results in performance of a calculation according to equations 6 and or 7, supra. Such computing devices include computer chips of any type (EPROM, etc.), CPUs, personal and mainframe computers, etc. Thus the present invention includes flourescence spectrometers (specrofluorometers) and other instruments that contain computing devices having programming that results in performance of a calculation according to the invention, and instrument-computer combinations that have programming that results in performance of a calculation according to the invention.

Figure 6:
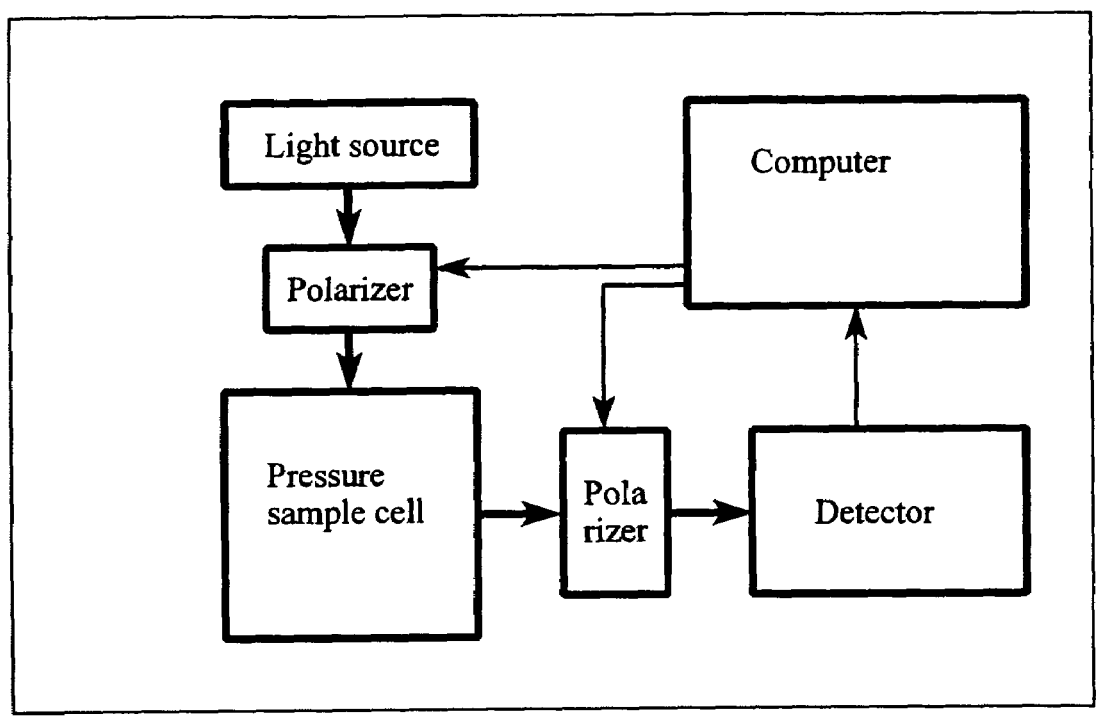
FIG. 6 is a block diagram of fluorescence spectrometer that may be adopted for fluorescence polarization anisotropy and intensity measurements in accordance with the present invention.

FIG. 6 is a block diagram of fluorescence spectrometer that may be adopted for fluorescence polarization anisotropy and intensity measurements in accordance with the present invention. Polarizers must be able to polarize light in such a way, that the plane of electric field vector of this light is perpendicular (V orientation) or parallel (H orientation) to the plane of drawing.

Typically, the Pressure sample cell is equipped with a cuvette containing a sample of interest and pressure-resistant windows for transmission of excitation and fluorescence light. High hydrostatic pressure (typically up to 3 kbar and higher) may be applied inside this cell. Preferably, the light source emits a monochromatic excitation beam. It is highly desirable to know the degree of depolarization of this light (E). The detector typically will incorporate any of a number of dispersive devices that select the wavelength of fluorescent light for detection and convert the light to an electronic signal. In accordance with preferred method of the invention, the grating factor (G), which represents inequality of sensitivities for both V and H polarization components of detected light, must be known for ever wavelength of interest.

It will be appreciated that each of the components depicted in FIG. 6, except for the computer, is standard equipment in most commercially available fluorometers. The computer is a device according to the present invention; i.e., it includes program code that performs the analyses described herein, for example extracting fluorescence anisotropies and intensities from data collected form the sample, which data are corrected for distortion by artifacts induced by pressure across the windows of the sample cell.

Figure 7:
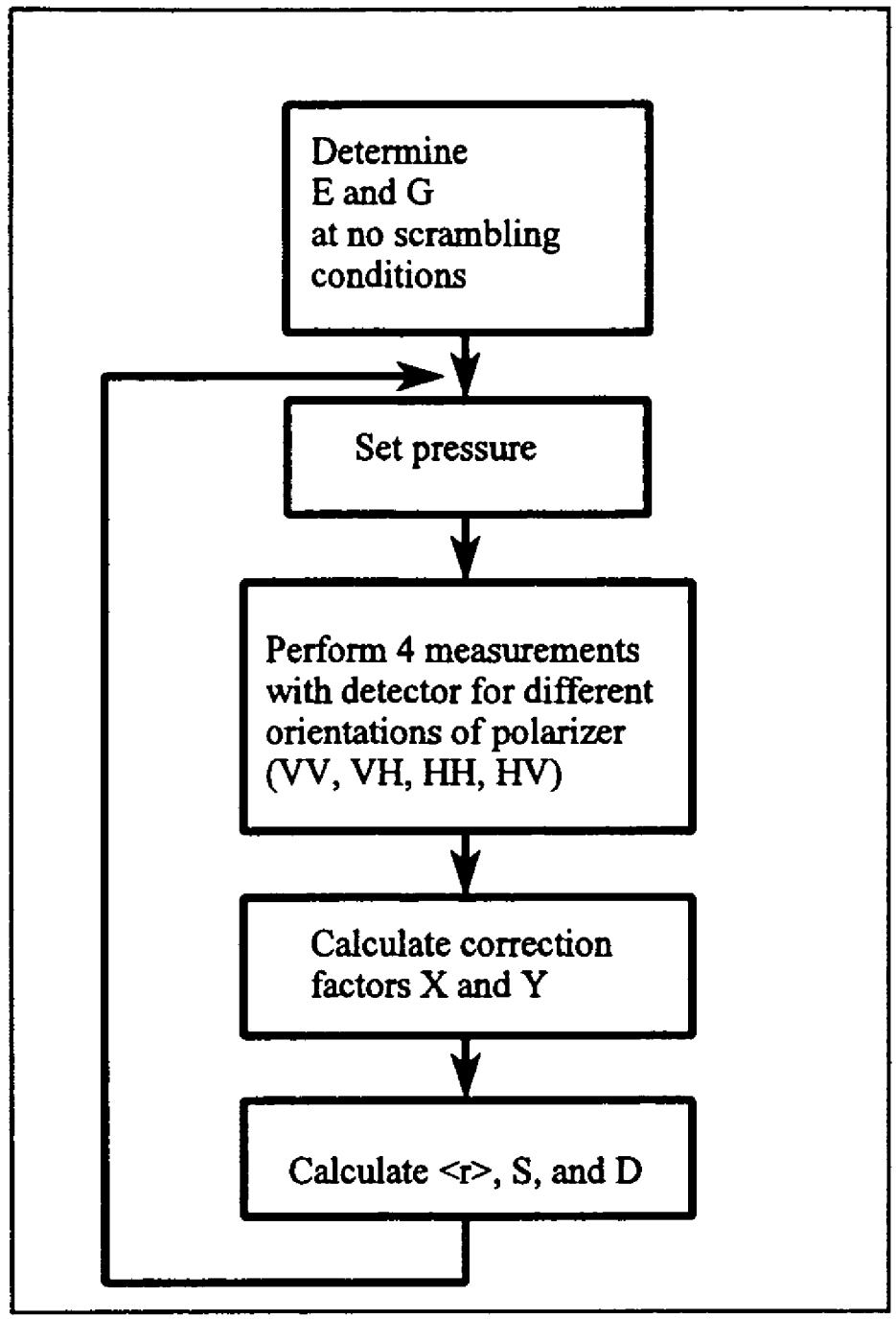
FIG. 7 is a block diagram depicting a typical determination of the corrected values of <r>, S and D.

Preferably, the computer also contains code enabling the automated collection of the polarized fluorescence data. FIG. 7 is a block diagram depicting a typical determination of the corrected values of <r>, S and D. Typically, the values for E and G are first determined at atmospheric pressure. A first give pressure is then set and achieved within the pressure cell, either manually or by automated equipment, which is commercially available. Four measurements of the fluorescence intensities are then obtained, reflecting all four combinations of the orientations (horizontal or vertical) of the emission and excitation polarizers. The two correction factors X and Y are then calculated. In preferred embodiments of the methods of the invention, <r>, S and D are then calculated, preferably using equations 2, 6 and 7, supra.

In a further aspect, the present invention also includes software that performs calculations according to the methods of the invention disclosed herein, and in particular, equations 2–7, supra.

Additional advantages and novel features of this invention will become apparent to those skilled in the art upon examination of the examples thereof provided below, which should not be construed as limiting the invention.

EXAMPLES

To demonstrate the versatility of the methods disclosed herein, corrections performed by the conventional 'second experiment' or indirect approach are compared below to those obtained by the methods of the invention. Corrections have been are performed on biologically challenging polarized data for the extrinsic fluorophore DPH imbedded within DPPC SUV bilayer membranes.

Example 1

The present method of correction has been tested for common fluorescent dyes 1,6-diphenyl-1,3,5-hexatriene (DPH) and 9,10-diphenylanthracene (DPA) in glycerol where their rotational behavior is well understood. In addition, the pressure induced>melt=profile for the more complicated biologically relevant system of DPH imbedded within dipalmitoylphosphatidylcholine (DPPC) small unilamellar vesicles (SUVs), has been reexamined.

Materials 9,10-Diphenylanthracene (DPA) was purchased from Aldrich Chemical Co. (Milwaukee, Wis.) and 1,6-diphenyl-1,3,5-hexatriene (DPH) was obtained from Molecular Probes, Inc. (Eugene, Oreg.). Both fluorescent dyes were used as supplied. Glycerol (Omnisolv; 99.84%) with UV cut-off of 203 nm, was purchased from EM Science (Gibbstown, N.J.). Absolute ethanol (200 proof; Gold Shield) was supplied by Commercial Solvents Corporation (Terre Haute, Ind.). L-α-dipalmitoylphosphatidylcholine (DPPC) was purchased from Sigma Chemical Company (St Louis, Miss.) and used without further purification. Lipid purity was checked using TLC analysis, as discussed elsewhere (See reference 22, infra.). Stock solutions of DPH in tetrahydrofuran (1 mM) and hexane (1 mM), and DPA in hexane (1 mM) were stored at 4° C. in the dark.

Glycerol solutions of DPH (4 µM) and DPA (4 µM) were prepared by evaporation of the appropriate volume of stock dye solution on to the walls of a small (25 mL) round bottomed flask. A gentle flow of nitrogen was used for evaporation of the organic solvents, followed by vacuum desiccation (p<1 mmHg). Glycerol (5 mL) was added to each flask, covered and swirled at ~40° C. overnight, using an incubator/shaker (New Brunswick Instruments, N.J.) to ensure complete dissolution of dye in glycerol. A hand-held (Fisher) UV lamp ($\lambda_{ex}$=366 nm) was used to check for the presence of any micro crystals of dye.

Small unilamellar vesicles (SUVs) of DPPC in 10 mM HEPES/5 mM KCl/140 mM NaCl, pH 7.4, were prepared by sonication and labeled with DPH (1:500; probe to phospholipid molar labeling ratio), using the method of direct solvent injection (See reference 23, infra.) as described in detail elsewhere (See reference 24, infra.). SUV preparations were maintained at temperatures above the lipid phase transition temperature ($T_c$=39° C.) (See reference 25, infra.) and used immediately for spectroscopic analysis. For fluorescence analyses, phospholipid concentrations (See reference 26, infra.) were typically less than 0.2 mM. Inner filter artifacts (See reference 27, infra.) were avoided by ensuring that the absorption of the fluorescent samples (here arising from the combination of both absorption from the dye plus vesicle scatter from the SUVs), at the wavelength of excitation, was less than 0.1.

Fluorescence Measurements

Steady state fluorescence emission anisotropy values, measured as a function of applied hydrostatic pressure, were recorded using a high pressure optical cell mounted in an SLM 8000 spectrofluorimeter, essentially as described elsewhere (See reference 9, infra.). The instrument was operated in the ratio mode to eliminate xenon lamp intensity fluctuations, and data collected using the analog rather than the photon counting mode.

A long-stemmed quartz cylindrical bottle was completely filled with the sample of interest and sealed using a Teflon stopper. Care was taken to ensure no air bubbles were trapped within the cuvette. The sample was loaded into the high pressure spectroscopy cell (equipped with quartz optical windows), filled with absolute ethanol (the pressure-transmitting fluid) and connected via high pressure stainless steel tubing to the transducing pump. The temperature within the high pressure spectroscopy cell was controlled using a water-circulating thermostatted jacket connected to a NesLab bath circulator. A temperature probe, inserted directly into the wall of the high pressure spectroscopy cell, provided constant measurement of the experimental temperature.

The four polarized fluorescence emission intensity components ($i_{VV}$, $i_{VH}$, $i_{HH}$ and $i_{HV}$) required for determination of EA values were measured as a function of increasing applied hydrostatic pressure using Glan Thompson polarizers, oriented either vertically or horizontally in the excitation or emission paths. Corrections of EA values for the pressure induced scrambling of the optical windows of the high pressure spectroscopy cell were achieved either using the indirect or direct method.

Data Analysis

Indirect Method: Correction for any birefringence of the quartz optical windows of the pressure cell was achieved using a scrambling factor ($\alpha$), determined essentially as discussed previously in detail by Paladini and Weber (See reference 14, infra), where:

$$\alpha = \frac{1}{3} \cdot \left[ 1 - \frac{<r>_{uncorr}}{<r>_{true}} \right] \quad (12)$$

Here $<r>_{true}$ represents the expected EA value with vertical excitation of a particular sample and $<r>_{uncorr}$ is defined in Equation (1). In analogy with the studies of Chong and Weber (See reference 9, infra.), we determined these EA values for DPH in glycerol (4 µM) at −10° C. Under these conditions, this rod-shaped dye, with collinear absorption and emission dipole oscillators is expected to be highly polarized with an EA value ($<r>_{true}$) approaching $r_0$=0.4. Measured EA values ($<r>_{uncorr}$) were then determined for the DPH/glycerol system as a function of increasing hydrostatic pressure, according to Equation (1). Depolarization of measured emission anisotropy values from the expected zero pressure values ($<r>_{true}$), arising as a result of pressure induced birefringence of the quartz optics and ethanol effects, provided estimates of the scrambling factor derived as a function of increasing hydrostatic pressure, $\alpha(p)$, (Equation (12)).

With a knowledge of the scrambling factors, $\alpha(p)$, EA values measured at a given applied pressure ($<r>_{uncorr}$), for any sample of interest may now be corrected ($<r>_{corr}$) through rearrangement of Equation (12):

$$<r>_{corr} = \frac{<r>_{uncorr}}{1 - 3 \cdot \alpha} \quad (13)$$

Direct Method: Here measured polarized emission intensities arising from the sample of interest are directly corrected for induced pressure-dependent birefringence scrambling effects. Values for E and G (the excitation and grating factors, respectively) were determined (for simplicity), using the sample of interest according to Equation (5), with p=1 bar. However, a more rigorous approach for determination of these factors requires measurement of an appropriate dye dissolved in an isotropic solvent (e.g. hexane or methanol), using the more conventional 10×10 mm square quartz cuvette under the same optical (excitation and emission) conditions as employed for the high pressure studies.

Subsequent values for X, Y and finally $<r>_{corr}$, for the experimental sample, measured as a function of hydrostatic pressure, were determined according to Equations (3), (4) and (5). After input of E and G, and for a given pressure the polarized emission intensities ($i_{VV}$, $i_{VH}$, $i_{HH}$, $i_{HV}$) for the sample of interest, the values of X(p) and Y(p) and then $<r>_{corr}$ can be retrieved automatically and directly.

RESULTS

FIG. 1A shows measured EA values ($<r>_{uncorr}$) for DPH imbedded in glycerol at 20° C. as a function of increasing pressure. Under these conditions, for p=1 bar, the relatively high EA value ($<r>_{p=1}$~0.35) confirms hindered rotational motions for this dye in glycerol at this temperature. However, with increasing applied hydrostatic pressure, rather than the expected increase in measured EA values (arising from effective reduction of the rotational volume for the dye), a significant decrease is observed. In the experimental set-up used for these studies, the excitation and emission polarizers are located before the optical windows, and outside of the high pressure spectroscopy cell. As a consequence, the depolarization effects observed arise primarily from pressure induced birefringence of the quartz excitation and emission windows, resulting in an effective>scrambling=of the polarized excitation and emission light. This effect becomes more serious for p>0.8 kbar. Indeed, at 2.0 kbar, measured EA values for DPH in glycerol are up to 20% less ($<r>_{uncorr}$~0.28) than the expected value ($<r>_{corr}$~0.36).

Using values for E and G (as defined in Equation 5) obtained from the same experiment at p=1 bar, measured polarized intensities for DPH in glycerol may be corrected, using the direct approach for such scrambling artifacts as discussed above (Equation 2). By solving for the excitation (X) and emission (Y) correction factors (FIG. 1B) values for $<r>_{corr}$ may then be calculated. The corrected data are shown in FIG. 1A, which now demonstrates the expected, albeit small, increase in $<r>_{corr}$ values for hindered DPH with increasing applied hydrostatic pressure. Interestingly, while the retrieved values for X(p) and Y(p) both increase with applied pressure, their values are not identical and at p>0.6 kbar, X(p) values are significantly higher than Y(p). This observation is perhaps not surprising, since the scrambling effects on the optical windows are dependent on both the wavelength of light transmission (see below), and their associated individual history (e.g., ageing, time of replacement) which can be quite different (See reference 28, infra.). That the scrambling correction factor can be resolved into the two contributing components (X and Y), now makes it possible to identify possible catastrophic events which may occur during the course of the experiment, the most common cause being the cracking of the quartz windows at high pressures. From the associated large anomalous alterations in the values of X or Y, it is possible to discern the particular pressure at which the window was affected.

Figure 2:
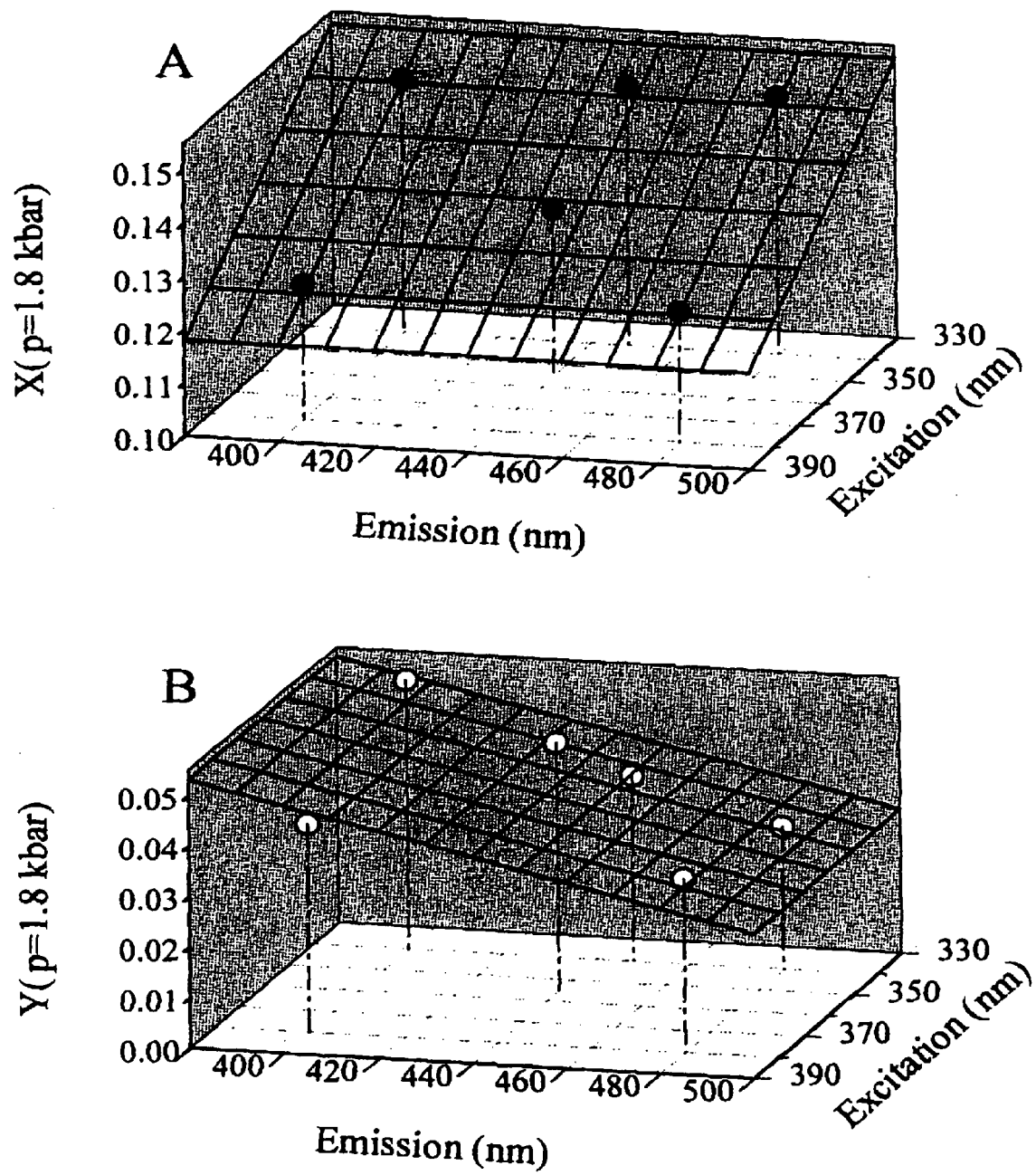
FIG. 2 shows the effect of wavelength on the excitation and emission correction factors at p=1.8 kbar for DPH in glycerol (4 μM) at 20° C. Panel A: Excitation correction factors (X(p=1.8) at 340, 355 and 380 nm) versus emission wavelength. Panel B: Emission correction factors (Y(p=1.8) at 400, 440 and 480 nm) as a function of excitation wavelength. Values for the excitation (E) and grating (G) factors were determined for the appropriate excitation and wavelength combinations from the same experiment, assuming X(p=1 bar)=0 and Y(p=1 bar)=0. Calculated errors were not greater than 0.005.

The effect of excitation and emission wavelength conditions on retrieved values of X(p) (excitation correction factor) and Y(p) (emission correction factor) for DPH in glycerol at p=1.8 kbar (where scrambling effects are large) are shown in FIG. 2. As previously discussed by Paladini and Weber (See reference 14, infra.), the average scrambling factor, $\alpha(p)$, is expected to depend on the chosen excitation and emission wavelength combination. This effect is clearly observed for retrieved values of X(p) and Y(p), measured as a function of excitation and emission wavelengths for DPH in glycerol (FIGS. 2A and B, respectively). In general, for the high pressure spectroscopy cell employed in these studies, X(p)>Y(p), although this can vary from instrument to instrument and from wavelength to wavelength. Values for the excitation correction factor, X(p) (FIG. 2A), decrease with increasing excitation wavelength and for a particular excitation wavelength are (as expected) independent of the emission wavelength. Similarly, values for the emission correction factor Y(p), are not dependent on the excitation wavelength (FIG. 2B). However, values generally decrease with increasing emission wavelength for a fixed excitation wavelength. Thus, while X(p) and Y(p) are separable variables, they are each intimately dependent on excitation and emission wavelength conditions, respectively, demonstrating larger values at shorter wavelengths. Hence when performing high pressure spectroscopic studies of intrinsic protein fluorescence, appropriate correction of EA values is a critical consideration.

Figure 3:
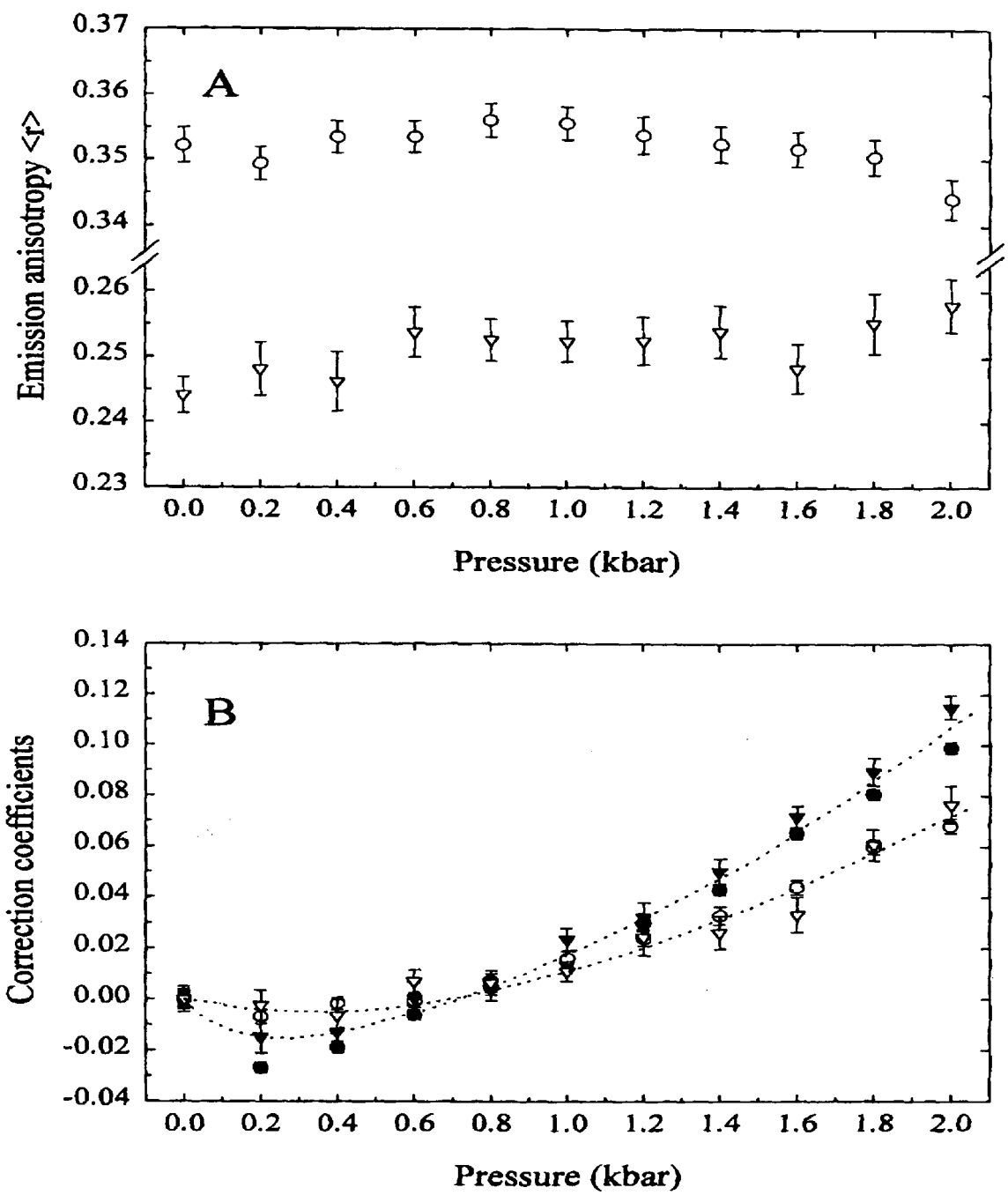
FIG. 3 shows the influence of the fluorescence dye on the excitation and emission correction factors. Panel A: Steady-state emission anisotropy (<r>) values corrected via the direct method, as a function of increasing applied hydrostatic pressure, for (○—○) DPH (4 μM) and ($\bar{\nabla}$-$\nabla$) DPA in glycerol (4 μM) at 20° C. Panel B: Excitation $(X(p)_{355\ nm})$ and emission $(Y(p)_{430\ nm})$ correction factors as a function of increasing hydrostatic pressure for DPH (●—● and ○—○, respectively) and DPA (▲—▲ and $\nabla$-$\nabla$, respectively). Values for the excitation (E) and grating (G) factors were determined for the appropriate experiments, assuming X(p=1 bar)=0 and Y(p=1 bar)=0. Excitation was 355 nm with emission detected at 430 nm, with corresponding bandwidths of 4 nm each, respectively. Calculated errors were not greater than 0.005.

FIG. 3 demonstrates that measured values for the correction factors, X(p) and Y(p) are, as expected, sample independent. Measurement of the EA for DPH and DPA in glycerol, under identical excitation (355 nm) and emission (430 nm) wavelengths, results in very similar values for the X(p) factors and similarly for the Y(p) pair, although differences between X(p) and Y(p) values are clearly visible (FIG. 3B). After direct correction of the measured EA values using the appropriate X(p) and Y(p) values, the $<r>_{corr}$ values obtained for the two dyes (FIG. 3A) provide the expected values and are indicative of very different anisotropic rotational behavior. For these studies, E and G values were determined using the respective dye/glycerol samples, with the pressure cell at p=1 bar.

Figure 4:
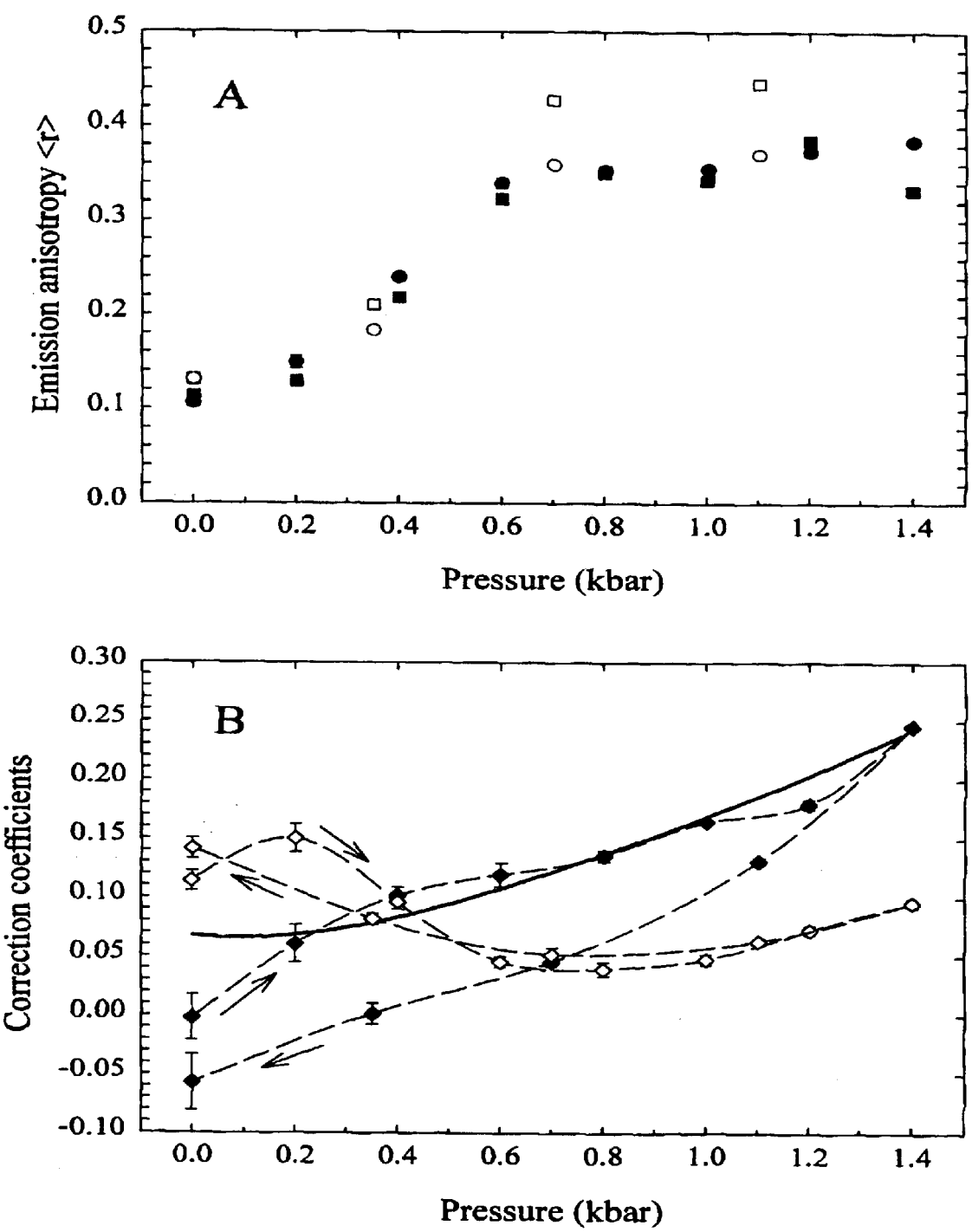
FIG. 4 shows DPH labeled DPPC SUVs (1:500 probe to phospholipid molar labeling ratio) at 50.3° C. Panel A: Steady-state emission anisotropy (<r>) corrected either by the direct (circles) or indirect (squares) methods, as a function of increasing (●—● and ■—■, respectively) and decreasing (○—○ and □—□, respectively) hydrostatic pressures. For the indirect method, a value of $<r>_{true}$=0.39 [29] was employed. In the direct approach, values for the excitation (E=2.500±0.006) and grating (G=1.586±0.006) factors were determined in a separate experiment using DPH in hexane (1.1 μM). Panel B: Values for the excitation, $X(p)_{355}$ nm (♦—♦) and emission, $Y(p)_{430}$ nm (◇—◇) correction factors as a function of increasing or decreasing applied hydrostatic pressure (direction shown by the arrows). Excitation was 355 nm and emission recorded at 430 with corresponding bandwidths of 4 nm each, respectively. The solid line represents the α(p) correction factor used for correction of pressure scrambled polarized data by the indirect method using DPH in glycerol at −10° C., and determined using increasing pressure conditions. Calculated errors were not greater than 0.005.

Application of the direct fitting model for correction of pressure-polarized intensity data of a complex biological system is shown in FIG. 4. Here a pressure 'melt' curve (EA versus applied hydrostatic pressure) is shown for DPH labeled DPPC SUVs at 50.3° C., where at p=1 bar the phospholipid exists in the fluid phase. The E and G-factors were determined from DPH in hexane using identical excitation and emission wavelength conditions as employed for the SUV sample (355 nm; 430 nm). Additionally, for this example, the data was also corrected using the indirect method, where the $\alpha(p)$ scrambling factors were determined in a separate experiment employing DPH in glycerol at −10° C., as discussed in the Methods section. As shown (FIG. 4), the two methods of polarized data correction provide the same end result, exhibiting the characteristic sigmoidal increase in the measured EA values for lipid imbedded DPH with increasing applied pressure corresponding to a pressure induced fluid-to-gel lipid transition and consequent reduction in the rate of dye rotation within the more rigid lipid matrix. At 50.3° C., the midpoint for the phase transition ($P_m$) is ~0.5 kbar. When using the direct method for correction of EA values however, a separate experiment for determination of the scrambling factors is not required, and the correction is performed on the experimental data directly.

Interestingly, also shown are the EA data for DPH imbedded in SUVs after release of the applied hydrostatic pressure. Correction of EA values using the indirect ($\alpha(p)$) method clearly shows a hysteresis in the measured data, with values for $<r>_{corr}$, after release of the applied pressure, exceeding the theoretical maximum value of $r_0$=0.4 achievable for DPH (See references 9, 29, infra.). However, if the direct correction approach is adopted, both increasing and decreasing pressure EA data ($<r_{corr}>$) are super-imposable, with no evidence of hysteresis in the data (FIG. 4A). Investigation of the values for the correction factors X(p) and Y(p) (FIG. 4B) provide insights into the origins of this disparity arising from the two methods employed for correction of this polarization data. Although Y(p) values show little sensitivity to the increase and decrease of applied pressure for the high pressure spectroscopy cell used in these studies, X(p) values do reveal hysteresis, giving rise to the observed anomalous reverse pressure EA data as shown in FIG. 4A where the same $\alpha(p)$ values are used for both increasing and decreasing pressure data. Hence, values for $\alpha(p)$ as determined from increasing the applied pressure are better suited for correction of measured polarized data obtained under the same conditions, i.e., in this case, increasing applied pressure.

The effect of pressure induced scrambling on the total fluorescence intensity ($i_{tot}$) was assessed via numerical simulation (FIG. 5). Under conditions where the total intensity measurement is independent of instrumental parameters as well as the fluorescence emission anisotropy, the instrumental readout is expected to be proportional (exclusively) to the quantum efficiency of the fluorophore.

For the simulations, the quantum efficiency of the fluorophore was assumed to be pressure independent and the measured intensity was normalized to an arbitrary value of 1.0 at r=0.1 and p=1 bar conditions. Observed deviations of the emission intensity from unity were assessed as a function of both varying the sample emission anisotropy value (0.1 to 0.36), and the scrambling coefficients (from zero at p=1 bar to values obtained experimentally as represented by the data shown in FIG. 4 at 1.4 kbar). Calculations were performed using the formalism described by Equation 6 (with a G-factor of 0.8), and Equations 8 through 12.

As expected, simulations performed at atmospheric pressure (X=0, Y=0), using no polarizer in the emission channel (conditions 1 & 2; FIG. 5A) with increasing sample emission anisotropy (from 0.1 to 0.36) results in distortions of the retrieved emitted light intensities. With appropriate orientation of excitation and emission polarizers according to >magic angle=conditions (FIG. 5A, conditions 3, 4 5 and 6), the correct total intensity values of unity are recovered regardless of the EA value. Similarly, intensity values determined from the sum (S) of polarized intensities (Equations (1) and (6)) provided the theoretically expected total intensity value (FIGS. 5A/5B; conditions 7, 8 and 9).

With application of pressure, all possible experimental geometries gave rise to incorrectly recovered total intensity values, particularly for the higher sample anisotropy values. The actual total intensity value recovered appears to depend on the method of determination used, with the best recovery obtained using simulations employing 'magic angle' conditions, and in particular those using depolarized excitation light (FIG. 5A, condition 2). However, in practice, non-polarized excitation light is very often difficult to achieve due to the inherent polarization of the excitation source. As expected, mathematical correction of pressure affected total intensity via Equation (6), provides the theoretically expected value (FIG. 5B, condition 9), although it must be emphasized that such simulations were made within the framework of the scrambling model discussed here and consequently other effects not accounted for, could be present in an actual experiment.

Example 2

Derivation of Equations

A.1. Standard Instrument Description: Polarized or partially polarized light may be completely described via a four component Stokes vector (See reference 30, infra.):

$$I = \begin{bmatrix} I \\ M \\ C \\ S \end{bmatrix} = I \cdot \begin{bmatrix} l \\ m \\ c \\ s \end{bmatrix} = \begin{bmatrix} <m_x^2(t) + m_y^2(t)> \\ <m_x^2(t) - m_y^2(t)> \\ <2m_x(t)m_y(t)\cos\delta> \\ <2m_x(t)m_y(t)\sin\delta> \end{bmatrix} \quad (A.1)$$

where $m_x$ and $m_y$ are amplitudes (with relative phase shift $\delta$) of the electric field in directions x and y, respectively. It is assumed that the x direction lies parallel with the experimental plane and will be referred to as the horizontal (H) component, whereas the y direction, perpendicular to the experimental plane, is assigned as vertical (V). It is also assumed that the absorption and subsequent fluorescence emission of a fluorophore arise exclusively from electric dipole transitions and are not sensitive to any rotations by the electromagnetic field. Furthermore, it is assumed that the fluorescence instrument considered here is equipped with one rotating excitation polarizer and a similar one in the detection channel, and is therefore not sensitive to circular polarization effects. While this restriction may serve to make the result less general, it is applicable to most commonly used experimental configurations. In any case, any phase circular polarization components will not be taken into account and the phase shift ($\delta$) will be consistently assumed to be zero.

Under such conditions, the last component of the Stokes vector is always equal to zero. The intensity components $I_V$ and $I_H$, as defined above, are connected with the Stokes vector components as follows:

$$I_V = I\frac{l-m}{2}; \quad I_H = I\frac{l+m}{2} \quad (A.2)$$

A.2 Instrumental Considerations: A standard "L-format" instrument, which consists of: an excitation source; an excitation-path monochromator; a rotating polarizer on the excitation side; a high pressure spectroscopy cell (equipped with thick, quartz windows); a rotating emission polarizer; an emission-path monochromator; and a photodetector is assumed. A simplified mathematical representation for the photodetector signal (i) may be formulated for this standard instrument by defining certain factors:

a). The Light Source: The excitation light of desired wavelength $\lambda$, is often partially polarized as a result of inherent polarizing effects arising from the various instrumental components (e.g., lamp or laser, excitation monochromator). As a consequence, the emerging excitation light $I_0$ will generally comprise both vertical and horizontal components: $I_{0V}$ and $I_{0H}$. This polarization bias of the excitation beam before the excitation polarizer can be described by a (sample independent) factor E, defined as follows:

$$E = \frac{I_{OH}}{I_{OV}} \text{ or } E = \frac{l-m}{l+m} \text{ if } I_0 = I \cdot \begin{bmatrix} l \\ m \\ s \\ 0 \end{bmatrix} \quad (A.3)$$

Since both vertical and horizontal polarization components may now be selected via rotation of the excitation polarizer, it is desirable that the instrumental E factor is equal (or close) to unity.

b). Rotating Polarizers: An "ideal" linear polarizer which may be oriented at any angle $\gamma$ with respect to vertical transmission axis is assumed. The emerging polarized light intensity is now defined by the matrix POL($\gamma$)) given in Equation (A.4), multiplied by the vector for the incoming light (Equation (3)) (31).

$$POL(\gamma) = \frac{1}{2}\begin{bmatrix} 1 & -\cos(2\cdot\gamma) & \sin(2\cdot\gamma) & 0 \\ -\cos(2\cdot\gamma) & \cos^2(2\cdot\gamma) & -\cos(2\cdot\gamma)\cdot\sin(2\cdot\gamma) & 0 \\ \sin(2\cdot\gamma) & -\cos(2\cdot\gamma)\cdot\sin(2\cdot\gamma) & \cos^2(2\cdot\gamma) & 0 \\ 0 & 0 & 0 & 0 \end{bmatrix} \quad (A.4)$$

If γ=0°, this permits transmission of the vertical excitation component only and the emergent light can be described by the vector $I_V\{1,-1,0,0\}$ and for γ=90°, the excitation polarization vector becomes $I_H\{1,1,0,0\}$.

c. Emission train: This usually consists of a polarizer (with polarized transmission intensities described by Matrix (A.4)), a light detector, and usually a monochromator. The latter component often demonstrates a preferential response sensitivity to one of the polarization components. This effect is described by the well known 'G-factor' (See reference 17, infra.). Hence, the measured response (i) of the detector to the approaching light can be described (within the proposed matrix framework) via a light detector operator, D(I) which acts on the light vector, I (Equation (A.1) as follows:

$$i = D(I) = \frac{1}{2} \cdot \beta \cdot Tr \left[ \begin{bmatrix} 1+G^{-1} & 0 & 0 & 0 \\ 0 & 1-G^{-1} & 0 & 0 \\ 0 & 0 & 0 & 0 \\ 0 & 0 & 0 & 0 \end{bmatrix} \cdot \begin{bmatrix} I \\ M \\ C \\ S \end{bmatrix} \right] \quad (A.5)$$

where Tr is the matrix trace operator and the β factor represents the light/photocurrent yield.

d. Sample chamber: It is assumed that:
(i) the sample has quantum yield Φ;
(ii) the excitation and emission beams are at 90° (L-format);
(iii) only electric dipolar transitions occur;
(iv) and if the fluorophore is excited by completely polarized light, the anisotropy of the emission is equal to r.

For these conditions, the fluorescence intensity (FL(r)) resulting from excitation by light I may be represented by:

$$FL(r) \cdot I = \Phi \cdot \begin{bmatrix} \frac{1}{3} \cdot (2-\frac{r}{2}) & -\frac{r}{2} & 0 & 0 \\ -\frac{r}{2} & \frac{r}{2} & 0 & 0 \\ 0 & 0 & 0 & 0 \\ 0 & 0 & 0 & 0 \end{bmatrix} \cdot \begin{bmatrix} I \\ M \\ C \\ S \end{bmatrix} \quad (A.6)$$

The first two rows of the FL(r) matrix can be easily calculated according to Crutzen et al. (See reference 32, infra, at Equation (10a)). The third row of the matrix must contain zeros for symmetry reasons: the fluorescence light component C of the Stokes vector (A.1) must be equal to zero since all amplitudes of the excitation light lie coplanar with the direction of observation ("L" format geometry—point ii above). Therefore, all "distribution cones" of the fluorescence transition moments have their main axis in this plane and inversion symmetry, with regards to the observation direction, is implied. The last row of the FL(r) matrix also contains zeros as previously defined by the electric dipole transition condition for the sample. A more general formalization of FL(r) will be published elsewhere.

The 'standard' polarization experiment, which consists of four measured photocurrent responses ($i_{VV}$, $i_{VH}$, $i_{HH}$, and $i_{HV}$), may now be represented as the product of the excitation (Equation A.4), sample response (Equation A.6) and emission (Equation A.4) matrices converted to a photocurrent response through the light detection operator (Equation A.5):

$$i_{VV} = D(POL(0) \cdot FL(r) \cdot POL(0) \cdot I_0)$$

$$i_{VH} = D(POL(\pi/2) \cdot FL(r) \cdot POL(0) \cdot I_0)$$

$$i_{HH} = D(POL(\pi/2) \cdot FL(r) \cdot POL(\pi/2) \cdot I_0)$$

$$i_{HV} = D(POL(0) \cdot FL(r) \cdot POL(\pi/2) \cdot I_0) \quad (A.7)$$

From Equation (A7), derivation of Equation (1) now follows.

A.3 Correction for Pressure Induced Effects: For polarized experiments performed under high pressure conditions, a special spectroscopy sample cell, equipped with thick (usually quartz) windows, is employed. As a result of strain-induced anisotropy (photoelastic) effects on the window material under pressure, a pressure-dependent scrambling of measured fluorescence polarized intensities arises. As discussed previously by Paladini and Weber (See reference 14, infra.), this effect may be represented, for vertically polarized incident light $I_{V0}$, by a scrambling coefficient $\alpha_V$, where:

$$I_V = (1-\alpha_V) \cdot I_{V0}$$

$$I_H = \alpha_V \cdot I_{V0} \quad (A.8)$$

By analogy, a similar expression can be written for horizontally polarized incident light using $\alpha_H$, as the scrambling coefficient. In matrix notation, the scrambling effect can be expressed as:

$$\begin{bmatrix} 1 & 0 & 0 & 0 \\ \alpha_H - \alpha_V & 1-(\alpha_V+\alpha_H) & 0 & 0 \\ 0 & 0 & \sqrt{1-2\cdot\alpha_V}\cdot\sqrt{1-2\cdot\alpha_H} & 0 \\ 0 & 0 & 0 & \sqrt{1-2\cdot\alpha_V}\cdot\sqrt{1-2\cdot\alpha_H} \end{bmatrix}$$

It is not unreasonable to assume axial symmetry for the scrambling effect, where $\alpha_V = \alpha_H$. For such cases the scrambling matrix simplifies to:

$$SCR(\alpha) = \begin{bmatrix} 1 & 0 & 0 & 0 \\ 0 & 1-2\cdot\alpha & 0 & 0 \\ 0 & 0 & 1-2\cdot\alpha & 0 \\ 0 & 0 & 0 & 1-2\cdot\alpha \end{bmatrix} \quad (A.10)$$

In the approach of Paladini and Weber (See reference 14, infra.), α is assumed to be wavelength independent and thus represents a combination of both the excitation and emission scrambling effects. As shown here (see data presented in FIG. 2), this assumption may not be appropriate for many systems of interest.

Scrambling effects generated separately by either the excitation and/or emission windows may however, be resolved by assigning individual wavelength dependent scrambling factors to the excitation (X) and emission windows (Y). Under these conditions, utilizing definitions (A.5), (A.4), (A.6), (A.10) and (A.3), the photocurrent response for a pressure dependent polarized experiment may be written as:

$$i_{\gamma_{ex},\gamma_{em}}=D(POL(\gamma_{em}) \cdot SCR(Y) \cdot FL(r) \cdot SCR(X) \cdot POL(\gamma_{ex}) \cdot I_0) \quad (A.11)$$

On substituting $\gamma_{ex,em}=0$ or $\pi/2$, the four standard photocurrent responses may be defined:

$$G \cdot i_{VV} = \frac{1}{6} \cdot \beta \cdot \Phi \cdot I_0 \cdot (1-m) \cdot \quad (A.12)$$
$$(1+2 \cdot r - 3 \cdot X \cdot r - 3 \cdot Y \cdot r + 3 \cdot X \cdot Y \cdot r)$$

$$i_{VH} = \frac{1}{6} \cdot \beta \cdot \Phi \cdot I_0 \cdot (1-m) \cdot (1-r+3 \cdot Y \cdot r - 3 \cdot X \cdot Y \cdot r)$$

$$i_{HH} = \frac{1}{6} \cdot \beta \cdot \Phi \cdot I_0 \cdot (1+m) \cdot (1-r+3 \cdot X \cdot Y \cdot r)$$

$$G \cdot i_{HV} = \frac{1}{6} \cdot \beta \cdot \Phi \cdot I_0 \cdot (1+m) \cdot (1-r+3 \cdot X \cdot r - 3 \cdot X \cdot Y \cdot r)$$

Although the constant term $[\beta \Phi I_0]$ is unknown, three independent variables (X, Y and r) can be resolved. Equations (A.12) are solved symbolically using MATHCAD 6+ (MathSoft Inc.) for X, Y, and r, with substitution of the 'm' component of the Stokes vector by our E-factor (Equation A.3). Exact solutions are summarized in the Theory section and shown as Equations (2) through (5).

A.4. Important Considerations

Point 1: Since the final equations (A.12) are nonlinear, their solutions represented by Equations (2) through (5), may not be not unique. However, many simulations using varying scrambling factors (X,Y) and sample conditions (r) have been performed, all of which reduce to these solutions. For conditions where $<r>_{true}$ is close to zero for the sample, the coefficients X and Y are unresolvable. Hence, for practical purposes where $<r>_{true}<0.01$ for the sample of interest, the direct method for correction of scrambled polarized intensities and hence EA values, as determined from inputting values for X and Y, are unreliable. Under these limiting conditions, the indirect method, or Equation (10) is more appropriately employed for correction of the pressure induced "scrambled" polarized data.

Point 2: From Equations (3) and (4) and (5) it is obvious that if during the experiment the following relationships hold:

$$\frac{i_{HH}(p)}{i_{HV}(p)} = G \text{ and } \frac{i_{HH}(p)}{i_{VH}(p)} = E$$

then no scrambling effects exist. Therefore, it is important to obtain 'true' values for E and G with some degree of precision (a standard deviation of less than 1% is desirable), which raises the issue of the most accurate method for their determination.

The simplest approach involves using polarized data measured for the sample of interest inserted directly within the HPSC at p=1 bar. In this manner, values for E and G are obtained from Equation 5, and X(p=1 bar)=0 and Y(p=1 bar)=0. However, often this approach leads to derived negative values for X and Y under conditions where p=~0.3 kbar, a condition which is inconsistent with Equation (A.7). Negative values for the correction factors is suggestive of possible residual scrambling effects, which arise from potential (and probably permanent) structural distortions of the optical window material resulting from repeated pressurization procedures. Alternatively, possible depolarization effects may result from internal reflections off the inner walls of the high pressure spectroscopy cell. Despite these effects, the assumption that X(p=1 bar) and Y(p=1 bar)=0 serves as a good first approximation in the estimation of true values for the factors E and G since errors involved in the recovered $<r>$ values are usually not significant.

An alternate approach for determining accurate values for the factors E and G involve the use of a standard square (10×10 mm) cuvette in place of the HPSC. Since E and G reflect the inherent optical properties of the spectrofluorimeter, it is expected that their value will be independent of the sample geometry employed. Standard thin-walled square quartz cuvettes are not expected to exhibit any scrambling artifacts arising from internal sample compartment reflections. However, E and G values determined using this optical configuration often lead to less consistent results than those obtained using the HPSC. Discrepancies most probably arise from unavoidable differences in the optical arrangements, e.g. light apertures.

Thirdly, estimation of E and G values is possible using a special isotropic sample, with r→0 (arising from a sample with a long fluorescence lifetime imbedded in a solvent of very low viscosity) rather than the sample of interest, in conjunction with the HPSC configuration at atmospheric pressure. Substituting r=0 into Equations (A.12) results in all terms within the parentheses equaling unity. Consequently, values for $$E = \frac{i_{HH}}{i_{VH}} \text{ and } G = \frac{i_{HH}}{i_{HV}}$$

can be estimated despite the unknown and non zero values for X and Y.

In general, adoption of a particular approach for the determination of E and G will depend on a particular experimental set up. However, often the first approach employing the HPSC and the sample of interest, is acceptable.

A.5 Total intensity measurements.

a. Extraction of total intensity data from polarized intensity measurements: The total intensity S, is expressed as: $S = G \cdot i_{VV} + 2 \cdot i_{VH}$ in the absence of scrambling. In general, the recorded photocurrent should be proportional to the product of the sample quantum yield ($\Phi$), excitation intensity $I_{0V}$, and detector sensitivity $\beta$. This product must be equal to some linear combination of $i_{VV}$ and $i_{VH}$:

$$\beta \cdot \Phi \cdot I_{0V} = A \cdot i_{VV} + B \cdot i_{VH} \quad (A.13)$$

Here, the factors A and B are sample (and EA) independent:

$$\frac{dA}{dr} = 0; \frac{dB}{dr} = 0.$$

On substituting Equation (A.12) into Equation (A.13), the following relationship for A and B is obtained under scrambling conditions:

$$A = G \cdot \frac{3 - B \cdot (1 - r + 3 \cdot r \cdot Y \cdot (1 - X))}{1 + 2 \cdot r - 3 \cdot r \cdot (X + Y - X \cdot Y)} \quad (A.14)$$

Differentiation of Equation (A.14) with respect to 'r' leads to the corrected formula for total fluorescence intensity (Equation (6)). Multiplication of Equations (2) and (6) results in Equation (7) or the difference in polarized emission intensities, under scrambling conditions.

b. Total Intensity Profiles Using 'Magic Angle' Conditions:
A measured signal proportional to the total fluorescence intensity (and independent of r) for a given sample may be obtained directly from the photocurrent response under conditions of no scrambling using 'magic angle' polarizer geometries. Under scrambling conditions, the photocurrent response is derived using the matrix approach as described above:

Method 1: (vertical excitation, 'magic angle' detection):

$$i = D(POL(\gamma_M) \cdot SCR(Y) \cdot FL(r) \cdot SCR(X) \cdot POL(0) \cdot I) \quad (A.15)$$

or $$i = \frac{1}{6} \cdot \beta \cdot \Phi \cdot I_0 \cdot (1 - m) \cdot \frac{1 + 2 \cdot G}{3 \cdot G} \cdot [1 - (X - Y + X \cdot Y) \cdot r]$$

Method 2: ('magic angle' excitation, vertical detection):

$$i = D(POL(0) \cdot SCR(Y) \cdot FL(r) \cdot SCR(X) \cdot POL(\gamma_M) \cdot I) \quad (A.16)$$

or $$i = \frac{1}{6} \cdot \beta \cdot \Phi \cdot I_0 \cdot \left(1 + \frac{1}{3} \cdot m + \frac{2\sqrt{2}}{3} \cdot C\right) \cdot \frac{1}{G} \cdot [1 + (X - Y - X \cdot Y) \cdot r]$$

Method 3: (unpolarized excitation, 'magic angle' to horizontal detection):

$$i = D(POL(\frac{\pi}{2} - \gamma_M) \cdot SCR(Y) \cdot FL(r) \cdot SCR(X) \cdot \{I_0, 0, 0, 0\}) \quad (A.17)$$

or $$i = \frac{1}{3} \cdot \beta \cdot \Phi \cdot I_0 \cdot \frac{2 + G}{3 \cdot G} \cdot \left[1 - \frac{1}{2} \cdot Y \cdot r\right]$$

Method 4: ('magic angle' to horizontal excitation, scramble plate detection or G=1):

$$i = D(SCR(Y) \cdot FL(r) \cdot SCR(X)POL(\frac{\pi}{2} - \gamma_M) \cdot I) \quad (A.18)$$

or $$i = \frac{1}{3} \cdot \beta \cdot \Phi \cdot I_0 \cdot \left(1 - \frac{1}{3} \cdot m + \frac{2\sqrt{2}}{3} \cdot c\right) \cdot \left[1 - \frac{1}{2} \cdot X \cdot r\right]$$

For all methods $$\gamma_m = \arccos\left(\frac{1}{\sqrt{3}}\right) = 54.736^0.$$

The measured photocurrent is always dependent on both the emission anisotropy (r) and the scrambling coefficients. These systematic errors are represented by terms shown in the square brackets.

REFERENCES CITED ABOVE

1. Markley, J. L., Northrop, D. B., and Royer, C. A. (1996) *High Pressure Effects in Molecular Biophysics and Enzymology*, Oxford University Press, New York.
2. Heremans, K., and Smeller, L. (1998) *Biochim. Biophys. Acta*. 1386, 353–370.
3. Gorovits, B. M., and Horowitz, P. M. (1998) *Biochemistry* 37 6132–6135.
4. Vidugiris, G. J., and Royer, C. A. (1998) *Biophys. J.* 75, 463–470.
5. Valente-Mesquita, V. L., Botelho, M. M., and Ferreira, S. T. (1998) *Biophys. J.* 75, 471–476.
6. Silva, J. L., Miles, E. W., Weber, G. (1986) *Biochemistry* 25, 5780–5786.
7. Bernsdorff, C., Wolf, A., Winter, R., and Gratton, E. (1997) *Biophys. J.* 72 1264–1277.
8. Beney, L., Perrier-Cornet, J. M., Hayert, M., and Gervais, P. (1997) *Biophys. J.* 72 1258–1263.
9. Chong, L. G., and Weber, G. (1983) *Biochemistry* 22, 5544–5550.
10. Targowski, P., and Davenport, L. (1998) *J. Fluorescence* 8, 121–128.
11. Sassaroli, M., Vauhkonen, M., Somerharju, P., and Scarlatta, S. (1993) *Biophys. J.* 64,137–149.
12. Chong, L-G., van der Meer, B. W., and Thompson, T. E. (1985) *Biochimica et Biophysica Acta*. 813, 253–265.
13. Lin, M. C. (1996) *Biochemistry* 10, 11846–11851.
14. Paladini, A. A. and Weber, G. (1981) *Rev. Sci. Instruments* 52, 419–427.
15. Sire, O., and Royer, C. A. (1996) *Biophys. J.*, 70, 2903–2914.
16. Jablonski, A. (1960) *Bulletin de L'Academie Polonaise des Sciences* 8, 259–264.
17. Chen, R. F. and Bowman, R. L. (1963) *Science* 147, 729–732.
18. Brand, L., Knutson, J. R., Davenport, L., Beechem, J. M., Dale, R. E., Walbridge, D. G., and Kowalczyk, A. A. (1985) Spectroscopy and the Dynamics of Molecular Biological Systems, (P. M. Bayley and R. E. Dale, editors), Academic Press, London. 259–305.
19. Beechem, J. M., Gratton, E., Ameloot, M., Knutson, J. R., Knutson, J. R., and Brand, L. (1991) Topics in Fluorescence Spectroscopy: Principles, (J. R. Lakowicz, ed.), Vol. 2, p. 241, Plenum, N.Y.
20. Davenport, L., Targowski, P., and Knutson, J. R. (1995) *Biophys. J.* 68, A58.
21. Chong P. L-G, and Cossins, A. R. (1983) *Biochemistry*, 22, 409–415.
22. Davenport, L., and Targowski, P. (1996) *Biophys. J.*, 71, 1837–1852.
23. Chen, L. A., Dale, R. E., Roth, S., and Brand, L. (1977) *J. Biol. Chem.* 252, 7500–7510.
24. Davenport, L. (1997) *Methods in Enzymology*, 278, (eds. L. Brand, and M. Johnson), 487–512, Academic Press.
25. Lentz, B. R., Barenholz, Y., and Thompson, T. E. (1976) *Biochemistry* 15, 4529–4537.
26. McClare, C. W. F. (1971) *Anal. Biochem.* 39, 527–530.
27. Weber, G., and Teale, F. W. J. (1957) *Trans. Farad. Soc.* 53, 646–655.
28. Cantor, D. M., Schroeder, J., and Jonas, J. (1975) *Applied Spectroscopy* 29, 393–396.
29. Kawato, S., Kinosita, K., Jr., and Ikegami, A. (1977) *Biochemistry* 16, 2319–2324.
30. Shurcliff, W. A. (1962) Polarized Light, Harvard Univ. Press, Cambridge, Mass.
31. Born, M., and Wolf, E. (1964) Principles of Optics, 2nd Ed, The MacMillan Company, New York, p. 554.
32. Crutzen, M., Ameloot, M., Boens, N., Negri, R. M., and DeSchryver, F. C. (1993) *J. Phys. Chem.* 97, 8133–8145.

Each of the foregoing references are incorporated herein by reference in their entirety. It is also intended that each of the other patents, applications, printed publications, and other published documents mentioned or referred to in this specification be herein incorporated by reference in their entirety.

Those skilled in the art will appreciate that numerous changes and modifications may be made to the preferred embodiments of the present invention, and that such changes and modifications may be made without departing from the spirit of the invention. It is, therefore, intended that the appended claims cover all such equivalent variations as fall within the true spirit and scope of the invention.

What is claimed is:

1. A process for measuring and removing scrambling effects induced by an applied hydrostatic pressure (p), from fluorescence intensities while avoiding the need for a separate pressurized calibration experiment, comprising the acts of measuring polarized fluorescence intensities and then determining excitation and emission correction factors simultaneously.

2. A process as recited in claim 1, wherein the act of determining excitation and emission correction factors simultaneously comprises the determination of excitation (X(p)) and emission (Y(p)) components, the respective values of which are dependent on hydrostatic pressure.

3. A process as recited in claim 2, wherein X(p) is given by:

$$X(p) = \frac{G \cdot i_{HV} - i_{HH}}{G \cdot i_{HV} - i_{HH} + E \cdot (G \cdot i_{VV} - i_{VH})}$$

wherein E and G are both sample and pressure independent instrument factors characteristic for the chosen excitation and emission wavelength conditions, and $i_{HV}$, $i_{HH}$, $i_{VV}$ and $i_{VH}$ are polarized fluorescence intensities.

4. A process as recited in claim 2, wherein Y(p) is given by:

$$Y(p) = \frac{E \cdot i_{VH} - i_{HH}}{E \cdot i_{VH} - i_{HH} + G \cdot (E \cdot i_{VV} - i_{HV})}$$

wherein E and G are both sample and pressure independent instrument factors characteristic for the chosen excitation and emission wavelength conditions, and $i_{VV}$, $i_{VH}$, $i_{HH}$, and $i_{HV}$ are polarized fluorescence intensities.

5. A method for the correction of time dependent polarized fluorescence intensities obtained for a sample under an applied hydrostatic pressure (p), comprising the steps of:
 a) collecting four non-truncated polarized $i_{VH}$, $i_{HH}$, $i_{HV}$) decay profiles;
 b) integrating said decay profiles;
 c) calculating emission and excitation correction factors X and Y, respectively, from integrals of said profiles; and
 d) using said emission and excitation factors, together with said $i_{VV}$ and $i_{VH}$ decay profiles, to perform a sum-difference analysis to obtain profiles for total corrected intensity ($S_{coff}$) and difference in polarized fluorescence intensity ($D_{coff}$).

6. The method of claim 5 wherein said correction is performed without performing a separate pressurized calibration experiment.

7. The method of claim 5 wherein said excitation correction factor X and said emission correction factor Y are determined for a given pressure (p) from said fluorescence intensities substantially according to the equations:

$$X(p) = \frac{G \cdot i_{HV} - i_{HH}}{G \cdot i_{HV} - i_{HH} + E \cdot (G \cdot i_{VV} - i_{VH})}$$

and:

$$Y(p) = \frac{E \cdot i_{VH} - i_{HH}}{E \cdot i_{VH} - i_{HH} + G \cdot (E \cdot i_{VV} - i_{HV})}$$

wherein $i_{VV}$, $i_{VH}$, $i_{HH}$, and $i_{HV}$ represent measured and distorted polarized intensities for the sample of interest, and E and G are both sample and pressure independent instrument factors characteristic for the chosen excitation and emission wavelength conditions.

8. The method of claim 6 wherein the E-factor corrects for any inequality in the intensities of the vertical and horizontal polarized excitation light, the G-factor corrects for unequal sensitivity the vertical and horizontal polarized emission light, and said E and G factors are determined at atmospheric pressure according to the equations:

$$G = \frac{i_{HH_0}}{i_{HV_0}}$$

and $$E = \frac{i_{HH_0}}{i_{VH_0}}$$

where said $i_{VH0}$, $i_{HH0}$, and $i_{HV0}$ are polarized fluorescence intensities obtained at atmospheric pressure.

9. The method of claim 8 wherein said difference in polarized fluorescence intensities ($D_{coff}$) is obtained substantially from the equation:

$$D_{corr} = G \cdot \frac{1}{1 - X - 2 \cdot (Y - X \cdot Y)} \cdot i_{VV} - \frac{1}{1 - X - 2 \cdot (Y - X \cdot Y)} \cdot i_{VH}$$

10. A computer-controlled instrument for measuring and removing scrambling effects, induced by an applied hydrostatic pressure (p), from fluorescence intensities while avoiding the need for a separate calibration experiment, comprising a computer/processor, a fluorescence spectrometer, and a computer readable storage medium comprising computer executable code for instructing the instrument to perform the acts of measuring polarized fluorescence intensities and then determining excitation and emission correction factors.

11. The computer controlled instrument of claim 10 wherein said excitation correction factor X and said emission correction factor Y are determined for a given pressure (p) from said fluorescence intensities substantially according to the equations:

$$X(p) = \frac{G \cdot i_{HV} - i_{HH}}{G \cdot i_{HV} - i_{HH} + E \cdot (G \cdot i_{VV} - i_{VH})}$$

and:

$$Y(p) = \frac{E \cdot i_{VH} - i_{HH}}{E \cdot i_{VH} - i_{HH} + G \cdot (E \cdot i_{VV} - i_{HV})}$$

wherein $i_{VV}$, $i_{VH}$, $i_{HH}$, and $i_{HV}$ and $i_{HV}$ represent the measured and distorted polarized intensities for the sample of interest, and E and G are both sample and pressure independent instrument factors characteristic for the chosen excitation and emission wavelength conditions.

12. The computer readable storage medium of claim 11 wherein the E-factor corrects for any inequality in the intensities of the vertical and horizontal polarized excitation light, the G-factor corrects for unequal sensitivity of a detection system of said fluorescence spectrometer to the vertical and horizontal horizontal polarized emission light, and said E and G factors are determined at atmospheric pressure according to the equations:

$$G = \frac{i_{HH_0}}{i_{HV_0}} \text{ and } E = \frac{i_{HH_0}}{i_{VH_0}}$$

where said $i_{VH0}$, $i_{HH0}$, and $i_{HV0}$ are polarized fluorescence intensities obtained at atmospheric pressure.

13. The computer readable storage medium of claim 10, further comprising the use of said excitation and emission correction factors to detect abnormalities in an optical window.

14. The computer readable storage medium of claim 12 wherein said true values of emission anisotropy ($<r>_{corr}$) are obtained from the equations:

$$<r>_{corr} = \frac{R - 1}{R + 2 - 3 \cdot (X + Y - X \cdot Y + R \cdot Y - R \cdot X \cdot Y)}; R = G \cdot \frac{i_{VV}}{i_{VH}}$$

15. The computer-controlled instrument of claim 14 wherein said true values of emission anisotropy are obtained from said fluorescence intensities without performing a separate pressurized calibration experiment.

16. The computer readable storage medium of claim 14, further comprising determining corrected total intensities ($S_{corr}$) in accordance with the following formula:

$$S_{corr} = G \cdot \frac{1 - 3 \cdot (Y - X \cdot Y)}{1 - X - 2 \cdot (Y - X \cdot Y)} \cdot i_{VV} + \frac{2 - 3 \cdot (X + Y - X \cdot Y)}{1 - X - 2 \cdot (Y - X \cdot Y)} \cdot i_{VH}$$

* * * * *